United States Patent
Yoshimine

(10) Patent No.: US 11,586,718 B2
(45) Date of Patent: Feb. 21, 2023

(54) AUTHENTICATION INFORMATION PROCESSING METHOD, AUTHENTICATION INFORMATION PROCESSING DEVICE, AND NON-TRANSITORY COMPUTER-READABLE MEDIUM

(71) Applicants: KABUSHIKI KAISHA DDS, Nagoya (JP); Kenji Miyoshino, Nagoya (JP)

(72) Inventor: Tatsuki Yoshimine, Nagoya (JP)

(73) Assignees: KABUSHIKI KAISHA DDS, Nagoya (JP); Kenji Miyoshino, Nagoya (JP)

( * ) Notice: Subject to any disclaimer, the term of this patent is extended or adjusted under 35 U.S.C. 154(b) by 542 days.

(21) Appl. No.: 16/678,522

(22) Filed: Nov. 8, 2019

(65) Prior Publication Data
US 2020/0074063 A1    Mar. 5, 2020

Related U.S. Application Data

(63) Continuation of application No. PCT/JP2018/016002, filed on Apr. 18, 2018.

(30) Foreign Application Priority Data

May 9, 2017    (JP) .............................. JP2017-093172

(51) Int. Cl.
*G06F 21/32*    (2013.01)
*G06K 9/62*    (2022.01)
(Continued)

(52) U.S. Cl.
CPC ........... *G06F 21/32* (2013.01); *G06K 9/6255* (2013.01); *G06T 7/00* (2013.01); *G06V 40/1365* (2022.01);
(Continued)

(58) Field of Classification Search
CPC ....... G06F 21/32; G06F 21/45; G06K 9/6255; G06T 7/00; G06T 7/0014; G06V 40/1365;
(Continued)

(56) References Cited

U.S. PATENT DOCUMENTS

2004/0096086 A1*  5/2004  Miyasaka .......... G06V 40/1306
                                                                    340/5.53
2004/0234111 A1   11/2004  Mueller
(Continued)

FOREIGN PATENT DOCUMENTS

CN    1125007 A    6/1996
CN    1487462 A    4/2004
(Continued)

OTHER PUBLICATIONS

Mar. 30, 2021 Office Action issued in Japanese Patent Application No. 2019-517535.
(Continued)

*Primary Examiner* — Mekonen T Bekele
(74) *Attorney, Agent, or Firm* — Oliff PLC

(57) ABSTRACT

An authentication information processing method for an authentication information processing device that includes a processor and a memory includes acquiring a plurality of pair candidate and image information for each of the plurality of pair candidate. The each of the plurality of pair candidate is a candidate of a combination of related information for collation and related information for registration to be used to calculate a degree of similarity. The authentication information includes a plural pieces of the related information. The method includes narrowing down the plurality of pair candidate by comparing the acquired image information of the plurality of pair candidate of the related information for collation and the related information for
(Continued)

registration and determining a correspondence between the related information for collation and the related information for registration used to calculate the degree of similarity, from among the narrowed down pair candidates.

15 Claims, 25 Drawing Sheets

(51) Int. Cl.
  *G06T 7/00* (2017.01)
  *G06V 40/50* (2022.01)
  *G06V 40/16* (2022.01)
  *G06V 40/12* (2022.01)
  *G06V 40/14* (2022.01)

(52) U.S. Cl.
  CPC ............ *G06V 40/172* (2022.01); *G06V 40/50* (2022.01); *G06V 40/14* (2022.01)

(58) Field of Classification Search
  CPC ...... G06V 40/172; G06V 40/50; G06V 40/14; G06V 40/1376; A61B 5/1172
  See application file for complete search history.

(56) References Cited

U.S. PATENT DOCUMENTS

| | | | |
|---|---|---|---|
| 2007/0003114 A1 | 1/2007 | Hendriks et al. | |
| 2007/0177767 A1 | 8/2007 | Miura et al. | |
| 2015/0347805 A1* | 12/2015 | McNulty | G06V 40/1312 382/124 |

FOREIGN PATENT DOCUMENTS

| | | |
|---|---|---|
| CN | 101011245 A | 8/2007 |
| CN | 104508675 A | 4/2015 |
| JP | H08-509562 A | 10/1996 |
| JP | 2004-102511 A | 4/2004 |
| JP | 2004-530217 A | 9/2004 |
| JP | 2007-504524 A | 3/2007 |
| JP | 2008-097097 A | 4/2008 |
| JP | 2012-133565 A | 7/2012 |
| JP | 2015-523876 A | 8/2015 |
| JP | 2017-010419 A | 1/2017 |
| KR | 10-2006-0123710 A | 12/2006 |
| WO | 2007/010209 A1 | 1/2007 |
| WO | 2015/164910 A1 | 11/2015 |

OTHER PUBLICATIONS

Jul. 17, 2018 Serach Report issued in International Patent Application No. PCT/JP2018/016002.
Jul. 17, 2018 Search Report issued in International Patent Application No. PCT/JP2018/016000.
Jul. 10, 2018 Search Report issued in International Patent Application No. PCT/JP2018/015999.
Jul. 17, 2018 Written Opinion of the International Searching Authority issued in International Patent Application No. PCT/JP2018/016000.
Jul. 17, 2018 Written Opinion of the International Searching Authority issued in International Patent Application No. PCT/JP2018/016002.
U.S. Appl. No. 16/678,451, filed Nov. 8, 2019 in the name of Yoshimine.
U.S. Appl. No. 16/678,348, filed Nov. 8, 2019 in the name of Yoshimine.
May 25, 2021 Office Action issued in Japanese Patent Application No. 2019-517534.
Jan. 16, 2021 Office Action issued in Korean Patent Application No. 10-2019-7034085.
Jan. 16, 2021 Office Action issued in Korean Patent Application No. 10-2019-7034071.
Jan. 9, 2021 Office Action issued in Korean Patent Application No. 10-2019-7034055.
Feb. 25, 2022 Non-Final Office Action Issued in U.S. Appl. No. 16/678,451.
Andrea R. Roddy et al., "Fingerprint Features-Statistical Analysis and System Performance Estimates", Proceedings of the IEEE, vol. 85, No. 9, Sep. 1997, pp. 1390-1421, INSPEC Accession No. 5714225, (Year: 1997).
Raoni F.S. Teixeira et al., "A New Framework for Quality Assessment of High-Resolution Fingerprint Images", IEEE Transactions on Pattern Analysis and Machine Intelligence, Oct. 2017; vol. 39, No. 10, pp. 1905-1917.
Sep. 20, 2022 Office Action issued in Chinese Patent Application No. 201880030072.7.
Dec. 1, 2022 Office Action issued in Chinese Patent Application No. 201880030066.1.

\* cited by examiner

FIG. 12

| | | | |
|---|---|---|---|
| 51 | ID:P14 | | |
| 52 | ATTRIBUTE INFORMATION | RADIAL INFORMATION:10001000:0x88 | |
| | | SURROUNDING INFORMATION:01100110:0x66 | |
| | | CLASSIFICATION INFORMATION:0x24 | |
| 53 | PERIPHERAL INFORMATION | 0 | ID:P13 |
| | | | ANGLE An0 |
| | | | DISTANCE D0 |
| | | 1 | ID:P2 |
| | | | ANGLE An1 |
| | | | DISTANCE D1 |
| | | ⋮ | ⋮ |
| | | 7 | ID:P24 |
| | | | ANGLE An7 |
| | | | DISTANCE D7 |

| | B1 (0x14) | B2 (0x33) | B3 (0x24) | B4 (0x24) | B5 (0x24) | B6 (0x25) | B7 (0x24) | B8 (0x25) | B9 (0x24) |
|---|---|---|---|---|---|---|---|---|---|
| A1 (0x24) | | | 94 | 55 | 68 | | 67 | | 48 |
| | | | 44 | 290 | 95 | | 165 | | 55 |
| A2 (0x14) | 85 | | | | | | | | |
| | 41 | | | | | | | | |
| A3 (0x24) | | | 10 | 87 | 47 | | 35 | | 54 |
| | | | 100 | 47 | 330 | | 285 | | 320 |
| A4 (0x24) | | | 32 | 37 | 9 | | 82 | | 36 |
| | | | 120 | 185 | 25 | | 46 | | 35 |
| A5 (0x33) | | 95 | | | | | | | |
| | | 45 | | | | | | | |
| A6 (0x25) | | | | | | 91 | | 7 | |
| | | | | | | 49 | | 270 | |
| A7 (0x24) | | | 19 | 56 | 80 | | 3 | | 49 |
| | | | 15 | 190 | 48 | | 10 | | 128 |
| A8 (0x24) | | | 33 | 4 | 59 | | 34 | | 84 |
| | | | 140 | 345 | 275 | | 255 | | 42 |
| A9 (0x25) | | | | | | 30 | | 92 | |
| | | | | | | 135 | | 40 | |
| A10 (0x24) | | | 90 | 7 | 5 | | 17 | | 22 |
| | | | 175 | 355 | 45 | | 210 | | 295 |

AUTHENTICATION INFORMATION PROCESSING METHOD, AUTHENTICATION INFORMATION PROCESSING DEVICE, AND NON-TRANSITORY COMPUTER-READABLE MEDIUM

CROSS REFERENCE TO RELATED APPLICATION

This application is a continuation application of International Application No. PCT/JP2018/016002, filed Apr. 18, 2018, which claims priority from Japanese Patent Application No. 2017-093172, filed on May 9, 2017. This disclosure of the foregoing application is hereby incorporated by reference in its entirety.

BACKGROUND

The present disclosure relates to an authentication information processing method, an authentication information processing device, and a non-transitory computer-readable medium that are configured to analyze an image and generate information used for collation of skin information.

Various fingerprint authentication devices are under consideration. For example, a known biometric identification device uses a pattern of ridges and troughs of a fingerprint extracted from biometric information and sweat pores extracted from the biometric information, and performs authentication of authentication information for collation with respect to authentication information for registration.

SUMMARY

In the known biometric identification device, sufficient consideration has not been given from the viewpoint of an improvement in authentication performance.

Various embodiments of the broad principles derived herein provide an authentication information processing method, an authentication information processing device, and a non-transitory computer-readable medium that are capable of improving authentication performance in comparison with related art.

Embodiments provide an authentication information processing method for an authentication information processing device that includes a processor and a memory. The authentication information processing method includes acquiring a plurality of pair candidate and image information for each of the plurality of pair candidate. The each of the plurality of pair candidate is a candidate of a combination of related information for collation and related information for registration extracted from the authentication information for collation and the authentication information for registration to be used to calculate a degree of similarity. The authentication information is used for biometric authentication, the authentication information including a plural pieces of the related information. Each of the plural pieces of the related information indicates relationship between a plurality of base points extracted in accordance with a predetermined condition from among a plurality of the base points extracted from an image and representing feature points of biometric information. The image information includes at least one selected from the group of a rotation amount and a movement amount between the image for collation and the image for registration calculated from the related information for collation and the related information for registration. The authentication information processing method includes narrowing down the plurality of pair candidate by comparing the acquired image information of the plurality of pair candidate of the related information for collation and the related information for registration. The authentication information processing method includes determining a correspondence between the related information for collation and the related information for registration used to calculate the degree of similarity, from among the narrowed down pair candidates.

Embodiments also provide an authentication information processing device that includes a processor and a memory. The memory is configured to store computer-readable instructions that, when executed by the processor, instruct the processor to perform processes. The processes include acquiring a plurality of pair candidate and image information for each of the plurality of pair candidate. The each of the plurality of pair candidate is a candidate of a combination of related information for collation and related information for registration extracted from the authentication information for collation and the authentication information for registration to be used to calculate a degree of similarity. The authentication information is used for biometric authentication, the authentication information including a plural pieces of the related information. Each of the plural pieces of the related information indicates relationship between a plurality of base points extracted in accordance with a predetermined condition from among a plurality of the base points extracted from an image and representing feature points of biometric information. The image information includes at least one selected from the group of a rotation amount and a movement amount between the image for collation and the image for registration calculated from the related information for collation and the related information for registration. The processes include narrowing down the plurality of pair candidate by comparing the acquired image information of the plurality of pair candidate of the related information for collation and the related information for registration. The processes include determining a correspondence between the related information for collation and the related information for registration used to calculate the degree of similarity, from among the narrowed down pair candidates.

Embodiments further provide a non-transitory computer-readable medium storing computer-readable instructions that are executed by a processor provided in an authentication information processing device, the computer-readable instructions, when executed, instructing the processor to perform processes. The processes include acquiring a plurality of pair candidate and image information for each of the plurality of pair candidate. The each of the plurality of pair candidate is a candidate of a combination of related information for collation and related information for registration extracted from the authentication information for collation and the authentication information for registration to be used to calculate a degree of similarity. The authentication information is used for biometric authentication, the authentication information including a plural pieces of the related information. Each of the plural pieces of the related information indicates relationship between a plurality of base points extracted in accordance with a predetermined condition from among a plurality of the base points extracted from an image and representing feature points of biometric information. The image information includes at least one selected from the group of a rotation amount and a movement amount between the image for collation and the image for registration calculated from the related information for collation and the related information for registration. The processes include narrowing down the plurality of pair candidate by comparing the acquired image information of the plurality of pair candidate of the related information for collation and the related information for registration. The processes include determining a correspondence between the related information for collation and the related information for registration used to calculate the degree of similarity, from among the narrowed down pair candidates.

BRIEF DESCRIPTION OF THE DRAWINGS

Embodiments of the disclosure will be described below in detail with reference to the accompanying drawings in which:

FIG. 12 is an explanatory diagram of the sweat pore-related information acquired for the central base point;

FIG. 21 is a chart showing combinations of the registration base points and the collation base points extracted as the pair candidates in the pair candidate extraction processing shown in FIG. 17, and a score and a rotation angle of each of the pair candidates;

DETAILED DESCRIPTION OF EMBODIMENTS

An embodiment of the present disclosure will be explained with reference to the drawings. Specific numerical values exemplified in the embodiment below are examples, and the present disclosure is not limited to these numerical values. In the explanation below, image data is simply referred to as an "image."

An authentication information processing device 10, which is common to first and second embodiments, will be explained with reference to FIG. 1. The authentication information processing device (hereinafter simply referred to as the "device") 10 is an electronic device that is provided with a function to generate, from biometric information (skin information), authentication information used for collation. The skin information is selected from biometric information represented by an image obtained by capturing an image of hairless skin, such as a finger, a palm, a sole of a foot and the like. The skin information of the present embodiment is a fingerprint and sweat pores. The device 10 of the present embodiment is a known smart phone. The device 10 is provided with functions to analyze an image obtained by capturing an image of a fingerprint and sweat pores, generate registration authentication information that is necessary for the collation using the skin information, and store the generated registration authentication information in a database (DB) 28 stored in a flash memory 4 of the device 10. The device 10 is provided with functions to analyze the image obtained by capturing the image of the fingerprint and the sweat pores, generate collation authentication information that is necessary for the collation using the skin information, and determine a correspondence between the generated collation authentication information and the registration authentication information stored in the DB 28.

Figure 1:
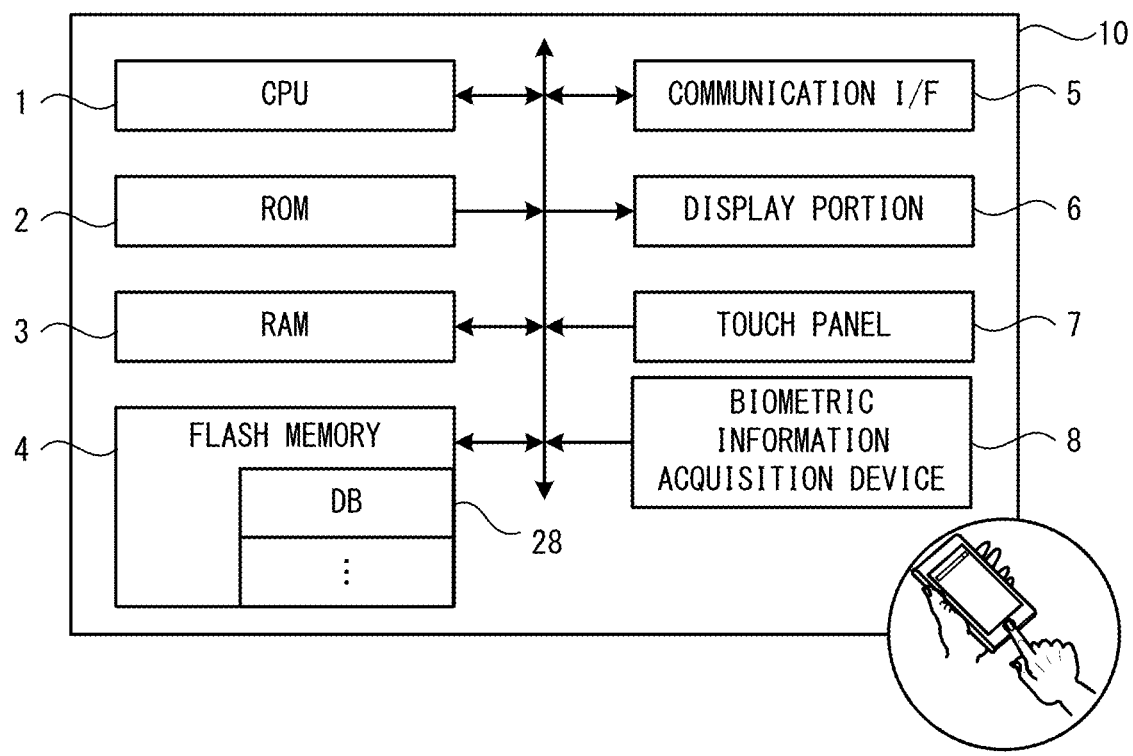
FIG. 1 is a block diagram of an authentication information processing device.

As shown in FIG. 1, the device 10 is provided with a CPU 1, a ROM 2, a RAM 3, the flash memory 4, a communication I/F 5, a display portion 6, a touch panel 7 and a biometric information acquisition device 8. The CPU 1 is a processor that performs control of the device 10. The CPU 1 is electrically connected to the ROM 2, the RAM 3, the flash memory 4, the communication I/F 5, the display portion 6, the touch panel 7 and the biometric information acquisition device 8. The ROM 2 stores a BIOS, a boot program and initial setting values. The RAM 3 stores various temporary data. The flash memory 4 stores a program that is executed by the CPU 1 to control the device 10, an operating system (OS) and the DB 28. The communication I/F 5 is a controller to perform communication with an external device. The display portion 6 is a liquid crystal display. The touch panel 7 is provided on the surface of the display portion 6. The biometric information acquisition device 8 acquires an image obtained by capturing an image of skin. The biometric information acquisition device 8 of the present embodiment is an area-type optical sensor or a microscope, and shows color information per pixel using 256 gray-scale values. The color information is information indicating color. It is preferable that the resolution of the image be equal to or more than 800 dots per inch (dpi), in order to acquire the image on which sweat pores can be identified. The resolution of the biometric information acquisition device 8 of the present embodiment is 2000 dpi, for example.

Authentication Information Processing of First Embodiment

Figure 2:
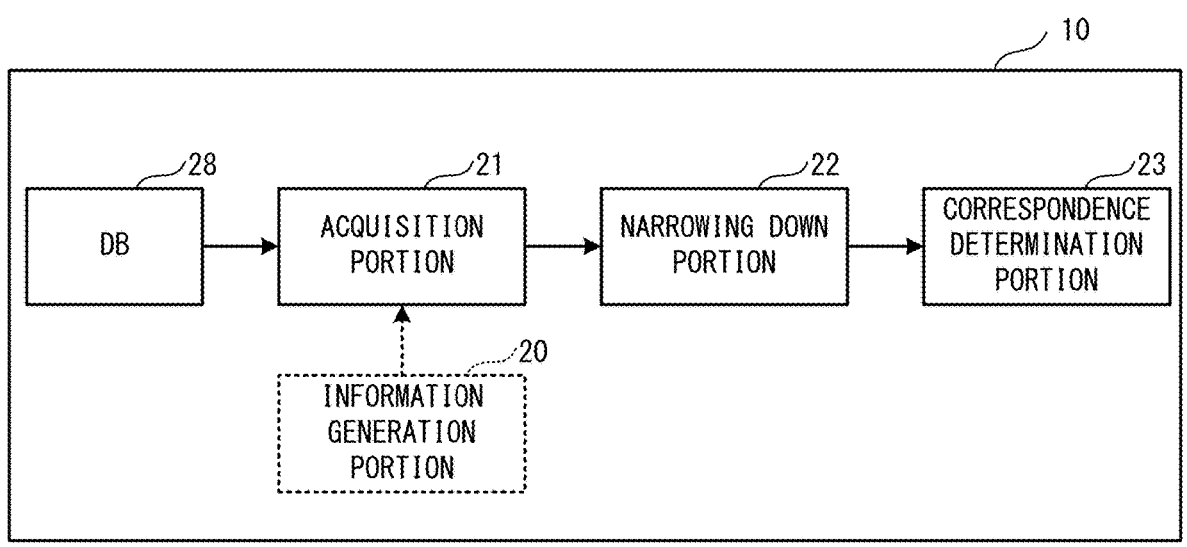
FIG. 2 is a functional block diagram of the authentication information processing device.

Authentication information processing that is performed in the device 10 of the first embodiment will be explained with reference to FIG. 2 to FIG. 6. As shown in FIG. 2, the device 10 includes the DB 28, an acquisition portion 21, a narrowing down portion 22 and a correspondence determination portion 23, and processing that corresponds to a functional block of each of these is performed by the CPU 1 (refer to FIG. 1).

Figure 3:
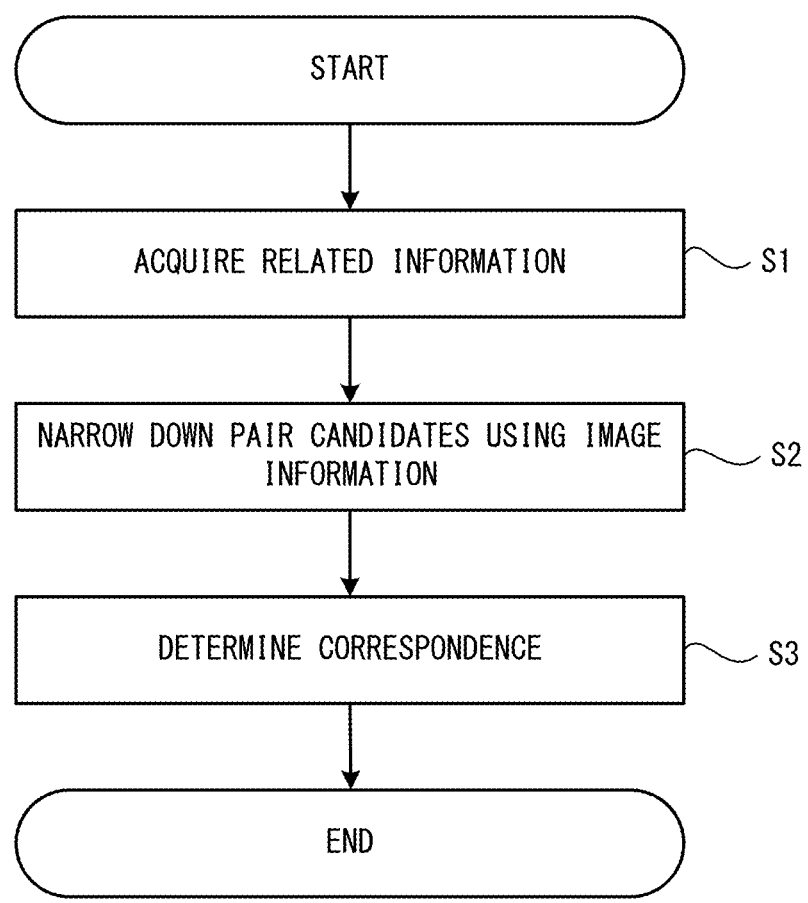
FIG. 3 is a flowchart of authentication information processing of a first embodiment.

As shown in FIG. 3, the acquisition portion 21 acquires combinations (pairs, correspondences) of related information for collation (hereinafter referred to as collation related information) and related information for registration (hereinafter referred to as registration related information) that are extracted as pair candidates, and a plurality of pieces of image information including at least one selected from the group of a rotation amount and a movement amount between a collation image and a registration image calculated from the collation related information and the registration related information (step S1). The related information is information indicating relationships between a plurality of base points extracted in accordance with a predetermined condition from among a plurality of the base points representing feature points of the biometric information. The pair candidates are candidates for combinations of the related information used to calculate a degree of similarity from the collation authentication information and the registration authentication information. The authentication information includes a plurality of pieces of the related information, and is information used for biometric authentication. More specifically, the related information of the present embodiment is information that associates attribute information with a central base point. When the base point that is a target of attention among the plurality of base points is set as the central base point and a predetermined number of the base points arranged around the central base point are set as peripheral base points, the attribute information is information indicating a feature of an arrangement on the image of each of the predetermined number of peripheral base points.

The related information may be information generated by the device 10, or may be information generated by another device and acquired by the device 10. The method for generating the related information may be set as appropriate. For example, when the biometric information is the skin information and the base points represent sweat pores on ridges of skin, the authentication information including the plurality of pieces of related information may be registration authentication information 34 and collation authentication information 94 exemplified in FIG. 4 and FIG. 5. The registration authentication information 34 includes related information 30 and related information 33. The related information 30 includes position information 31 and attribute information 32 of a base point A1. For example, the position information 31 is represented by two-dimensional coordinates 46 of an image coordinate system of an image 45 that represents the skin information shown in FIG. 5. Within the image 45 shown in FIG. 5, hatched regions show ridges, white regions show troughs between the ridges, and black circles show the base points that represent the sweat pores. For example, peripheral base points a0 to a7 are extracted with respect to the base point A1. For example, the peripheral base points a0 to a7 satisfy conditions that a distance from the base point A1 is less than a predetermined value and the number of the troughs between adjacent two of the ridges of the skin positioned between the central base point and each of the peripheral base points is equal to or less than 1. The attribute information 32 is information indicating the feature of the arrangement on the image of the peripheral base points with respect to the central base point. The attribute information is, for example, information that is set from the viewpoint of whether or not a target base point, which is the target of attention among the peripheral base points, is on the same ridge as the central base point or a particular peripheral base point. The attribute information may be, for example, information that is set from the viewpoint of at least one selected from the group of a distance and an angle between the target base point and the central base point or the particular peripheral base point. The attribute information may be information indicating one type of feature or may be a plurality of pieces of information indicating each of a plurality of types of feature.

The attribute information may include classification information, for example. The classification information includes first information indicating the number of the peripheral base points on the same ridge as the central base point, among the predetermined number of peripheral base points. When each of a predetermined number of line segments obtained by connecting the central base point and each of the predetermined number of peripheral base points is defined as a radial line segment, and when each of a predetermined number of line segments obtained by sequentially connecting, around the central base point, the peripheral base points on adjacent two of the radial line segments is defined as a surrounding line segment, the classification information includes second information indicating the number of the surrounding line segments on the ridges.

Figure 5:
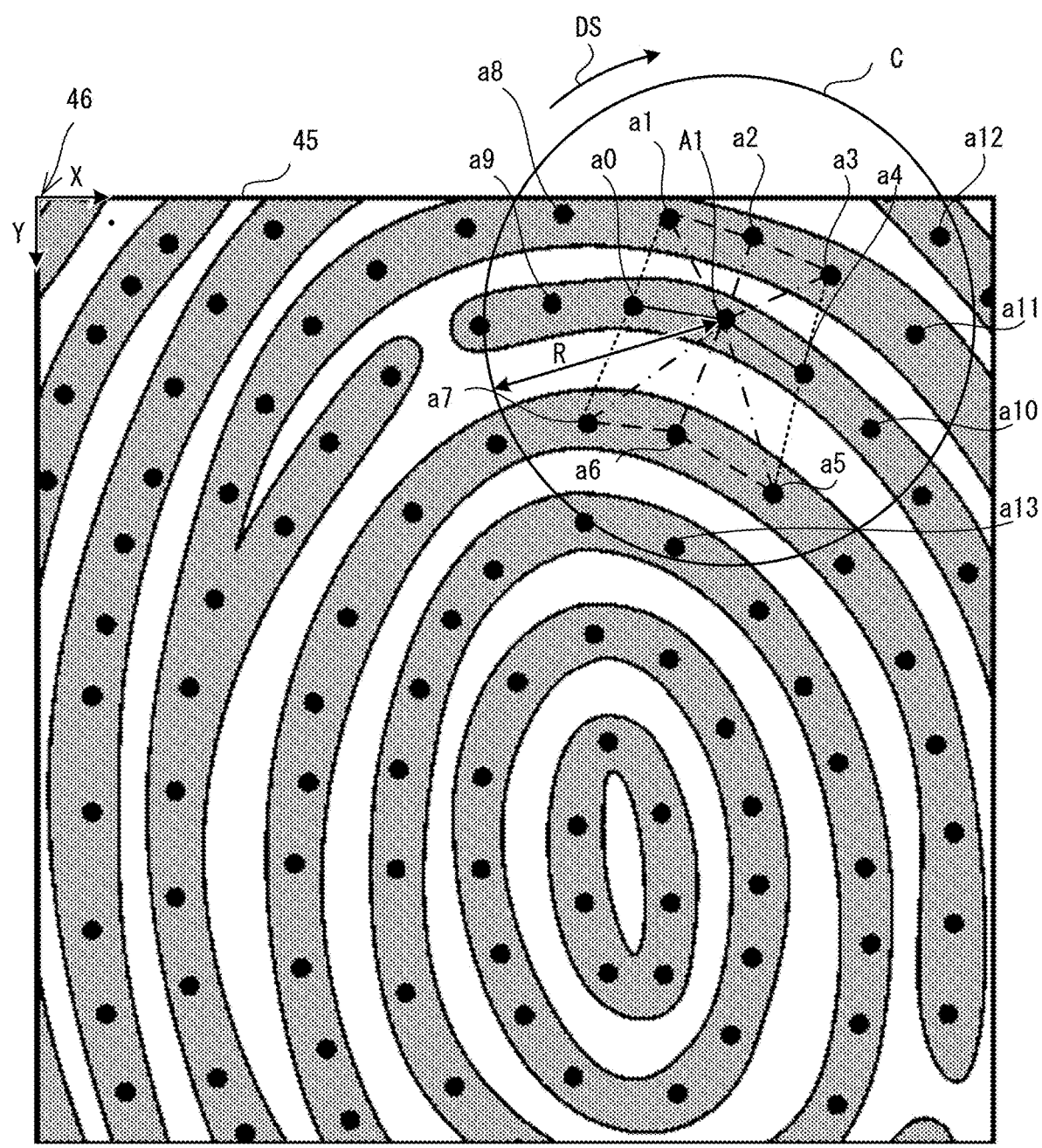
FIG. 5 is an explanatory diagram of the related information about base points.
Figure 6A:
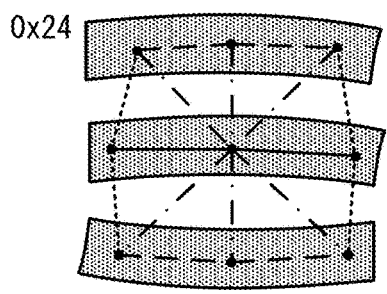
FIG. 6A to FIG. 6J are explanatory diagrams of pattern examples of attribute information.
Figure 6B:
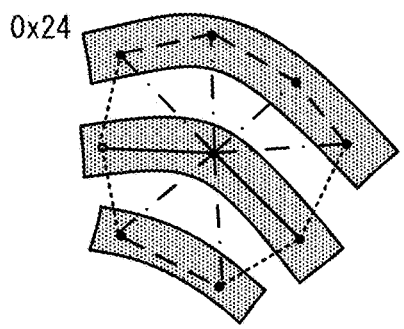
Figure 6C:
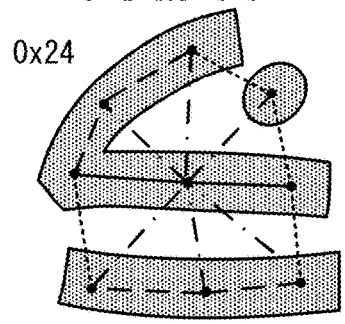
Figure 6D:
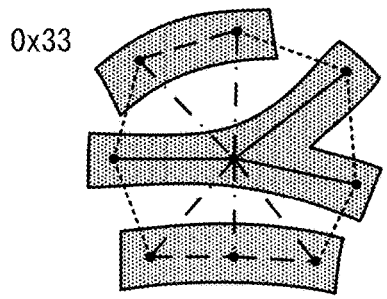
Figure 6E:
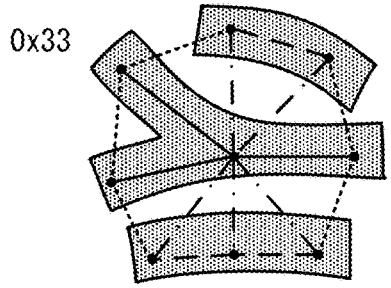
Figure 6F:
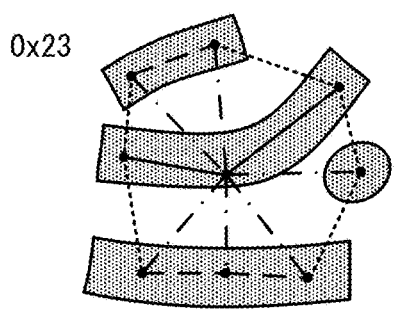
Figure 6G:
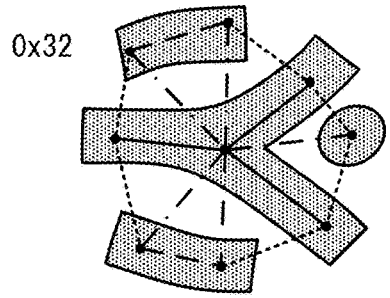
Figure 6H:
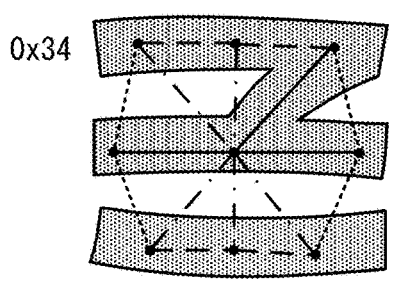
Figure 6I:
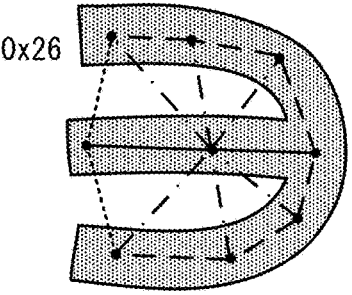
Figure 6J:
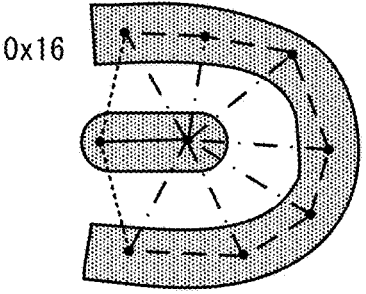

In FIG. 5, among the radial line segments obtained by connecting the central base point A1 and each of the peripheral base points a0 to a7, the radial line segments on the same ridge as the central base point A1 are denoted by solid lines, and the radial line segments that straddle the trough between the ridges are denoted by alternate long and short dash lines. With respect to the central base point A1, the number of the peripheral base points on the same ridge as the central base point is two. Among eight surrounding line segments obtained by sequentially connecting, around the central base point, the peripheral base points (of the eight peripheral base points a0 to a7 with respect to the central base point A1) that are on adjacent two of the radial line segments, the surrounding line segments on the ridges are shown by first dotted lines, and the surrounding line segments that straddle the trough are shown by second dotted lines that are finer than the first dotted lines. Therefore, among the eight surrounding line segments, the number of the line segments on the ridges is four. Therefore, the classification information is denoted by "0x24," for example. In "0x24," "0x" indicates a hexadecimal number, "2" indicates the number of the peripheral base points on the same ridge as the central base point (the first information), and "4" indicates the number of the surrounding line segments on the ridges (the second information). When the attribute information includes the classification information, as exemplified by the arrangement of the peripheral base points with respect to the central base point and the classification information in FIG. 6A to FIG. 6J, different pieces of the attribute information (the classification information) are obtained in accordance with the feature of the arrangement of the peripheral base points with respect to the central base point. In a similar manner, the collation authentication information 94 includes related information 90 and 93. The related information 90 of a base point B1 includes position information 91 and attribute information 92. The collation authentication information 94 is acquired from an information generation portion 20 provided in the device 10, for example. The information generation portion 20 generates the authentication information including the related information, on the basis of the image that represents the biometric information. As described above, the registration authentication information 34 and the collation authentication information 94 may be acquired from another device. It is sufficient that the image information includes at least one selected from the group of the rotation amount and the movement amount between the collation image and the registration image calculated from the collation related information and the registration related information. The image information of the present embodiment is the rotation amount calculated from the collation related information and the registration related information.

The pair candidates may be determined by the device 10, or may be determined by another device and acquired by the device 10. The method for determining the pair candidates may be set as appropriate. The acquisition portion 21 acquires combinations of the collation related information and the registration related information and a plurality of pieces of the image information, with respect to the pair candidates determined by the device 10 and registered in a list 39, for example.

Figure 4:
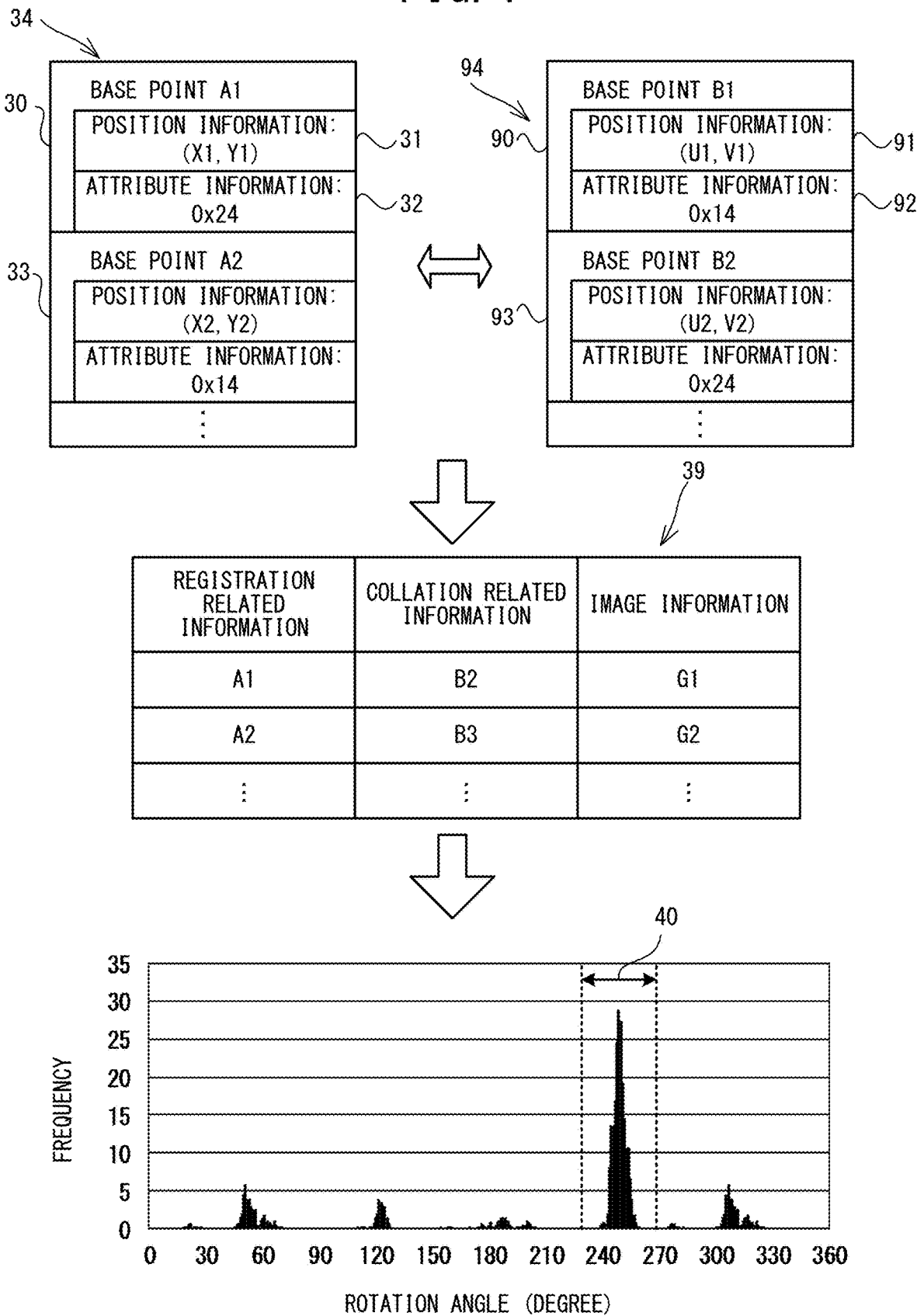
FIG. 4 is an explanatory diagram of a process that acquires related information and image information of pair candidates extracted from registration authentication information and collation authentication information.

The narrowing down portion 22 compares the information of the plurality of sets of combinations of the collation related information and the registration related information acquired at step S1, and narrows down the pair candidates (step S2). The method for narrowing down the pair candidates by comparing the image information may be set as appropriate. The narrowing down portion 22 of the present embodiment narrows down the pair candidates such that the image information thereof falls within a predetermined range that is set on the basis of a representative value of the image information of the plurality of sets of pair candidates acquired at step S1. More specifically, the narrowing down portion 22 narrows down the pair candidates according to the following procedure, for example. For example, as shown in FIG. 4, rotation angles of the pair candidates are classified into ranges per degree (a 360 resolution). When the range whose representative value is expressed as 249 degrees has the largest frequency, the narrowing down portion 22 extracts the pair candidates (the pair candidates within a range shown by arrows 40) whose image information falls within a plus/minus predetermined angle (20 degrees, for example) from the representative value 249 degrees, and narrows down the pair candidates to the extracted pair candidates.

The correspondence determination portion 23 compares the collation related information and the registration related information narrowed down by the processing at step S2, and determines a correspondence between the collation authentication information and the registration authentication information used to calculate the degree of similarity (step S3). For example, the correspondence determination portion 23 determines the correspondence by calculating a score using the collation related information and the registration related information. A known method may be used as the method for calculating the score. The CPU 1 ends the authentication information processing. The CPU 1 may use the correspondence between the collation authentication information and the registration authentication information determined at step S3 in processing that calculates the degree of similarity between the collation authentication information and the registration authentication information.

Authentication Information Processing of Second Embodiment

1. Processing at Time of Registration

Authentication information processing that is performed by the device 10 of the second embodiment will be explained with reference to FIG. 5 and FIG. 7 to FIG. 23, taking an example in which the authentication information is registered. The authentication information processing is started when a user inputs a start command. The start command includes a command relating to whether to register, in the DB 28, the authentication information acquired from the image as the registration authentication information, or whether to calculate the degree of similarity between the acquired authentication information and the registration authentication information registered in the DB 28. When the CPU 1 of the device 10 detects the input of the start command of the authentication information processing, the CPU 1 reads out, to the RAM 3, an authentication information processing program to execute the authentication information processing stored in the flash memory 4, and performs processing of respective steps to be described below, in accordance with instructions included in the authentication information processing program. In the present embodiment, feedback processing that prompts re-input is performed until the skin information that satisfies a requirement (for example, the brightness of the image) to extract the base points is acquired. The image acquired by the authentication information processing satisfies a requirement to extract the authentication information from the image using an algorithm. Information and data acquired or generated in the course of the processing are stored in the RAM 3 as appropriate. Various setting values that are necessary for the processing are stored in advance in the flash memory 4. Hereinafter, Step is Abbreviated to "S."

Figure 7:
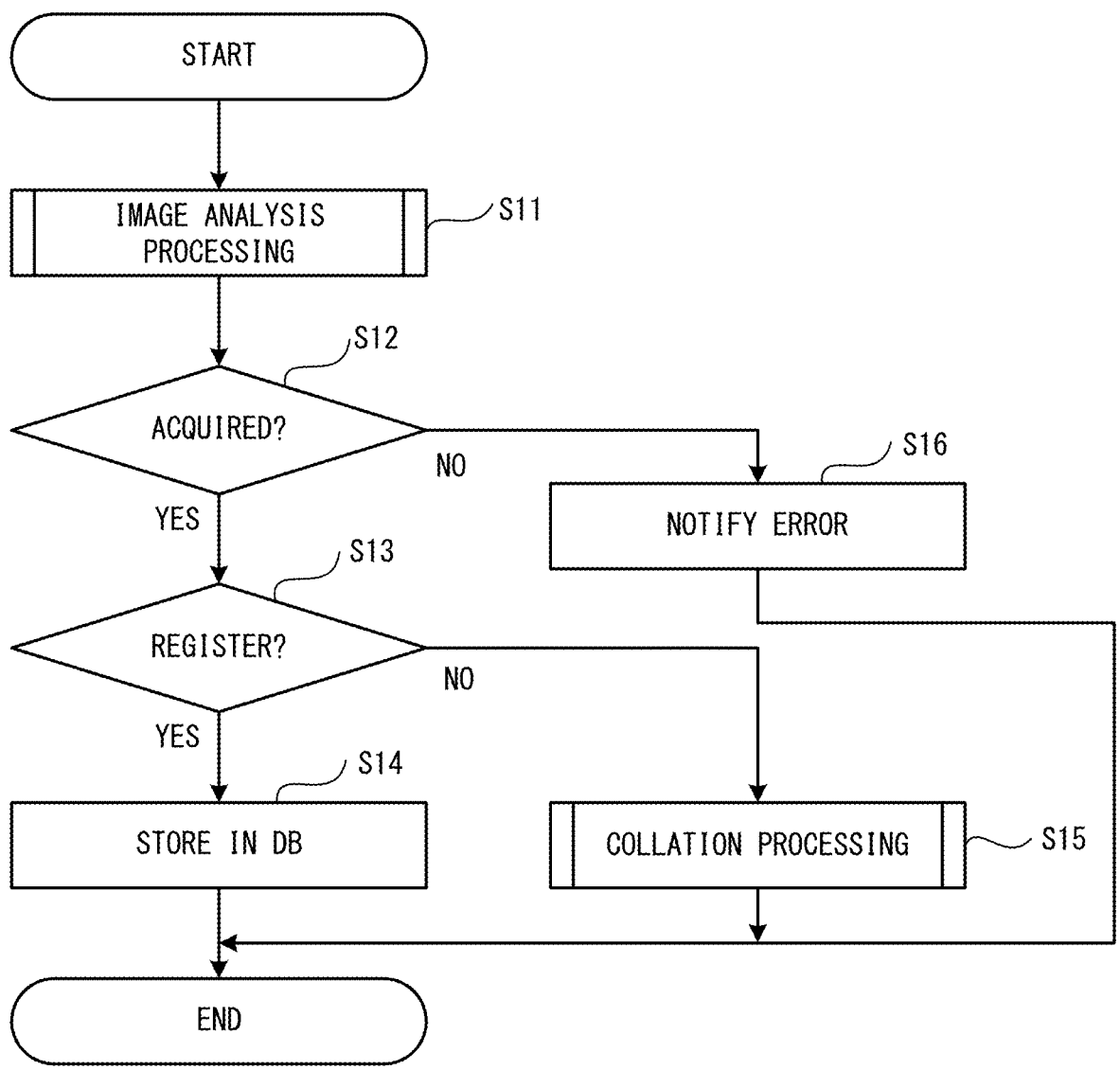
FIG. 7 is a flowchart of authentication information processing of a second embodiment.
Figure 8:
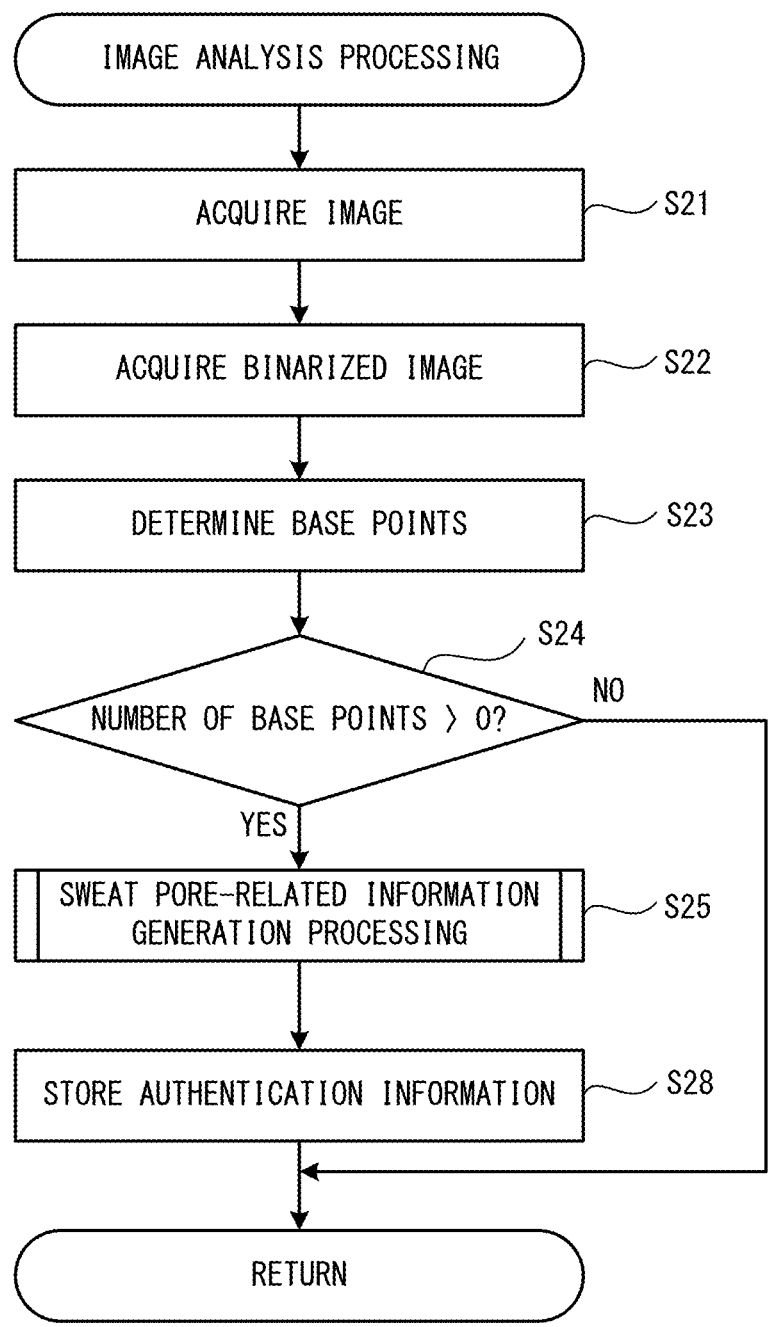
FIG. 8 is a flowchart of image analysis processing that is performed in the authentication information processing shown in FIG. 7.
Figure 9:
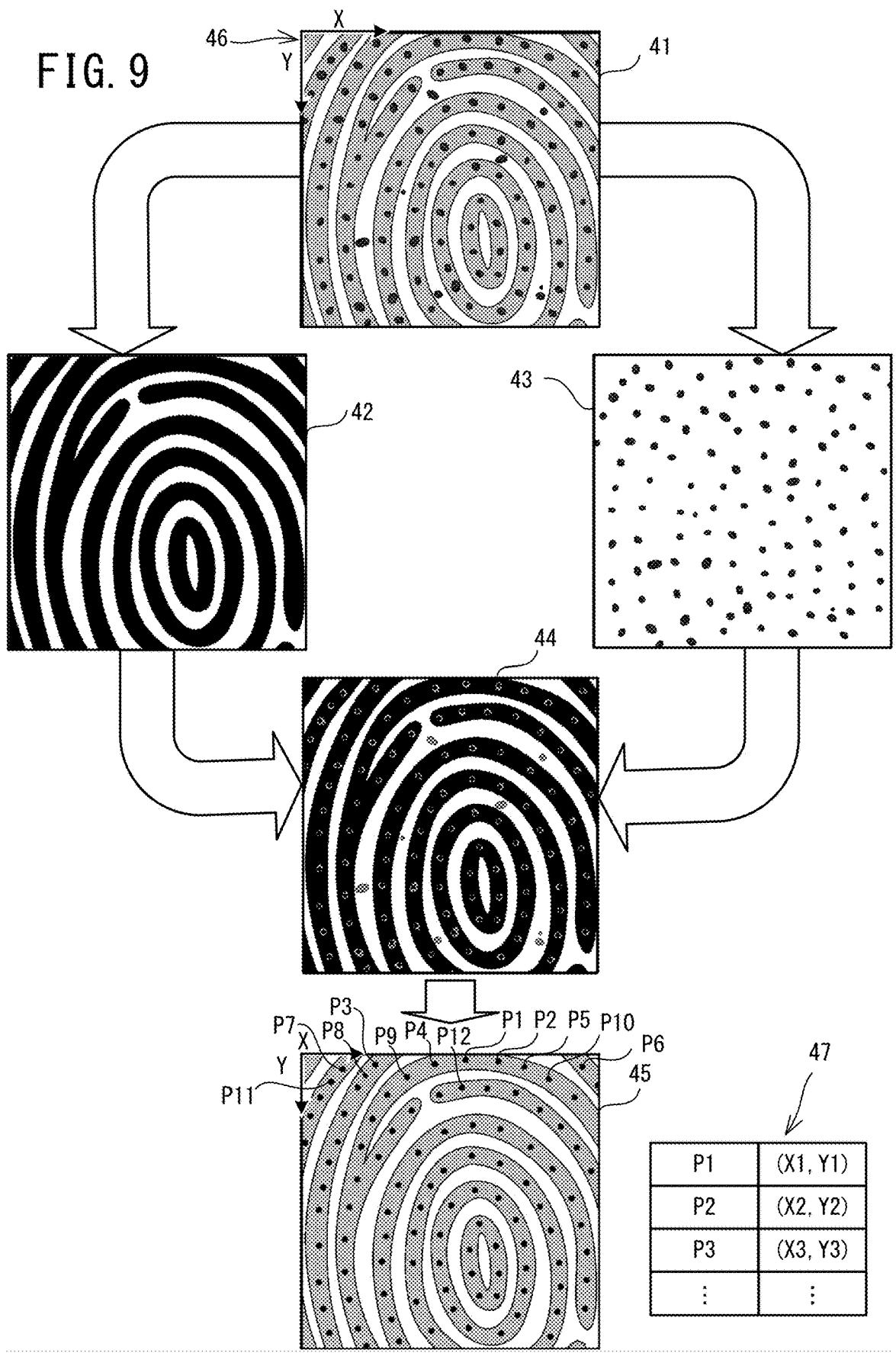
FIG. 9 is an explanatory diagram of a process that extracts base points on the basis of an image.

As shown in FIG. 7, the CPU 1 performs image analysis processing (S11). The image analysis processing will be explained with reference to FIG. 8. When a finger touch is detected, the biometric information acquisition device 8 outputs, to the CPU 1, a signal that can identify an image obtained by capturing the image of the fingerprint and the sweat pores. The CPU 1 receives the signal output from the biometric information acquisition device 8. The CPU 1 acquires the image on the basis of the received signal (S21). For example, the image 41 shown in FIG. 9 is acquired at S21. The two-dimensional coordinates 46 of the image coordinate system shown by X and Y are set in the image 41. The CPU 1 performs the binarization processing on the image 41 acquired at S21, and acquires the image 42 representing the ridges (S22). In another example, the image 42 may be obtained by applying the image 41 to a plurality of image processing filters that are used in processing of a minutia method. Within the image 42, black sections represent ridges and white sections represent sections of troughs between the ridges.

The CPU 1 determines the base points (S23). The CPU 1 applies the image 41 to the image processing filter that can extract the section of the particular range of gray values, acquires the image 43, and compares the image 42 and the image 43 by overlapping the images 42 and 43 as shown by the image 44. Thus, the CPU 1 identifies, as the sweat pores, the closed regions having the circular shape, the hook shape and the like that are disposed on the ridges indicated by the black sections. The CPU 1 determines the area centroid of each of the identified sweat pores to be the base point representing the sweat pore. The CPU 1 scans the image 45 from the left to the right and from the top to the bottom, in that order, and assigns the ID to each of the determined base points and acquires the position information. The position information of the present embodiment is coordinates in units of pixels of the two-dimensional coordinates 46 of the image coordinate system. The CPU 1 generates the list 47 indicating a correspondence between the assigned ID and the position information, and stores the list 47 in the RAM 3. The CPU 1 may determine whether or not to identify the sweat pores taking into consideration the size, shape and the like of the closed regions, as appropriate. In the present embodiment, a plurality of the base points including the base points P1 to P12 shown by black circles on the image 45 are determined. The CPU 1 determines whether or not the number of the base points determined at S23 is larger than 0 (S24). When the number of the base points determined at step S23 is 0 (no at S24), the CPU 1 ends the image analysis processing and returns the processing to the authentication information processing in FIG. 7. When the number of the base points determined at S23 is larger than 0 (yes at S24), the CPU 1 performs sweat pore-related information generation processing (S25). In the sweat pore-related information generation processing, processing to generate the sweat pore-related information, which associates the position information of the central base point with the attribute information, is performed for each of the plurality of base points.

Figure 10:
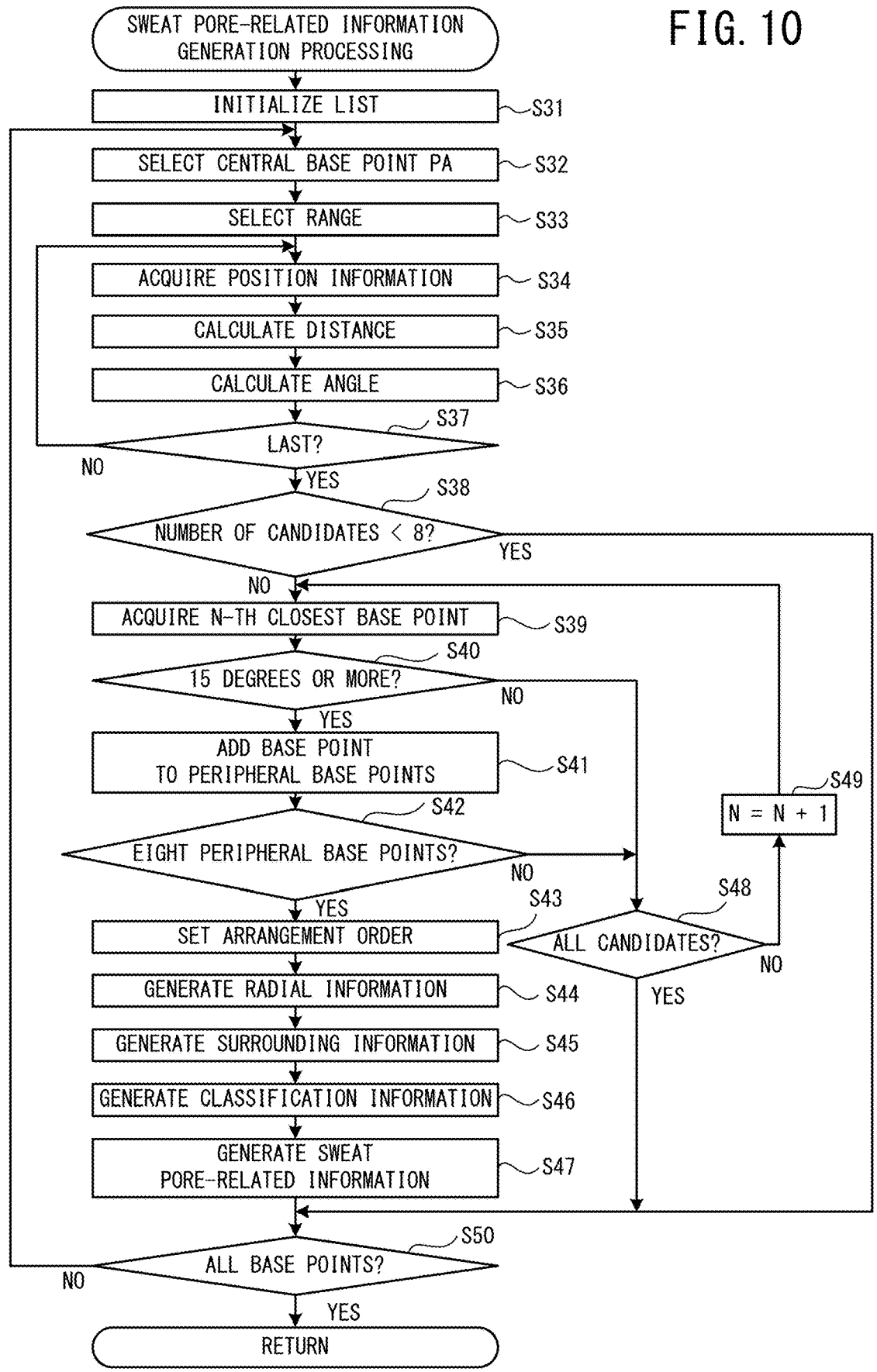
FIG. 10 is a flowchart of sweat pore-related information generation processing that is performed in the image analysis processing shown in FIG. 8.

As shown in FIG. 10, in the sweat pore-related information generation processing, the CPU 1 initializes a list to store the sweat pore-related information (S31). The CPU 1 selects, as a central base point PA, one of the plurality of base points determined by the processing at S23 in FIG. 8 (S32). Taking acquisition conditions of the peripheral base points into consideration, the CPU 1 may not select, as the central base point PA, the base point within a range in which the peripheral base points cannot be extracted. In the processing at S32, for example, the CPU 1 may not select, as the central base point, the base point within a range in which the distance from an end portion of the image 45 to the base point is less than half the predetermined value R to be described later. For example, the base point A1 on the image 45 shown in FIG. 5 is selected as the central base point. When one of the plurality of base points determined by the processing at S23 is selected as the central base point, on the basis of a predetermined condition, the CPU 1 performs processing to extract, as the peripheral base points, a predetermined number of the base points for which the distance from the central base point is less than a predetermined value R and the number of troughs between adjacent ridges of the skin positioned between the central base point and each of the predetermined number of base points is equal to or less than 1. The number of troughs between adjacent ridges of the skin positioned between the central base point and each of the predetermined number of base points is identified, for example, on the basis of the number of continuous white sections in the image 42 that exist between the central base point and each of the predetermined number of base points. The predetermined value R, the predetermined number and the predetermined condition are determined taking into consideration the distance between the sweat pores, the resolution of the image, authentication accuracy and the like. It is preferable that the predetermined value R be more than an average value H of the distances between the sweat pores and less than a value that is three times the average value H. It is preferable that the predetermined number be equal to or more than 4 and equal to or less than 15. Extraction conditions of the peripheral base points are, for example, that the predetermined value R is a radius R and the predetermined number is 8. The predetermined condition is, for example, a condition that selects, in ascending order of distance from the central base point, the predetermined number of base points for which an angle formed between a line segment connecting the central base point and the peripheral base point that has already been selected and a line segment connecting the central base point and the base point that is a candidate for the peripheral base point is equal to or more than a predetermined angle. When the predetermined number is 8, it is preferable that the predetermined angle be selected within a range from 5 degrees to 45 degrees, and the predetermined angle in the present embodiment is 15 degrees.

The CPU 1 refers to the list 47 and selects a range to extract candidates to be a peripheral base point PB from among the plurality of base points (S33). Specifically, the CPU 1 sets, as the range to extract the candidates to be the peripheral base point PB, a range in which the values of the Y coordinate of the two-dimensional coordinates of the base points stored in the list 47 are within plus or minus R of the Y coordinate of the central base point PA selected by the processing at S32. In the present embodiment, for example, from among the plurality of base points determined by the processing at S23, in order to acquire, as candidate base points PK, the base points whose distance (a Euclidean distance, for example) from the central base point PA is within the predetermined value R, the CPU 1 firstly selects the range over which to extract the candidates using the Y coordinates in the list 47.

From among the base points within the range selected by the processing at S33, the CPU 1 selects one of the base points (the target base point) that has not been selected at S34, and acquires the position information (S34). The position information is represented by the two-dimensional coordinates 46 of the image coordinate system. The CPU 1 calculates a distance between the central base point and the target base point on the basis of the position information acquired at S34 and the position information of the central base point selected at S32 (S35). A method for calculating the distance may be set as appropriate. The CPU 1 of the present embodiment calculates the Euclidean distance between the central base point and the target base point. For example, distances D0 to D7 are respectively calculated for the base points a0 to a7 in FIG. 5.

Figure 11:
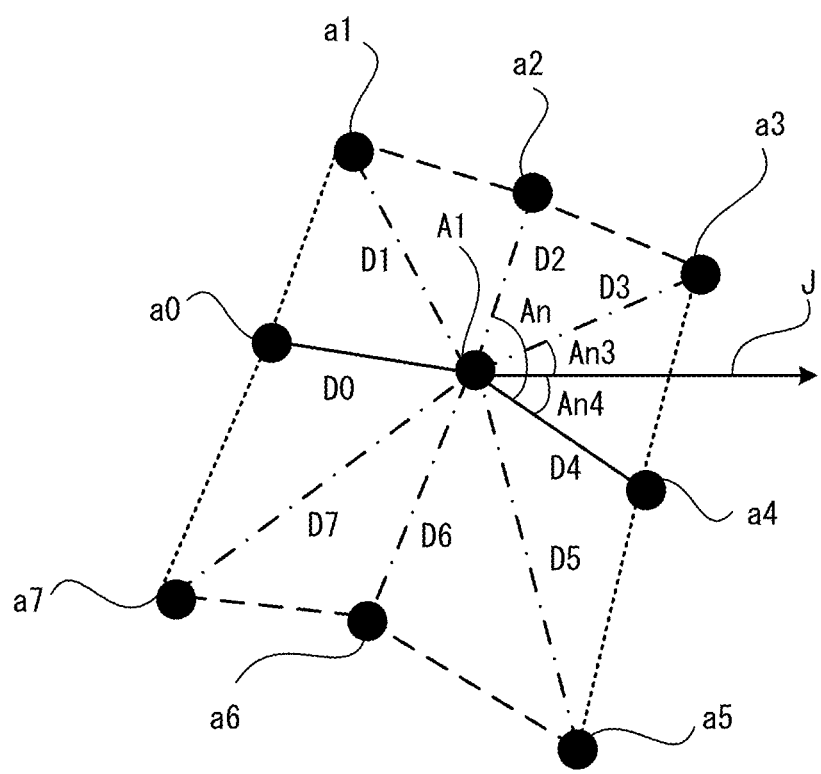
FIG. 11 is an explanatory diagram of a process that acquires the sweat pore-related information for a central base point.

The CPU 1 calculates an angle that represents an arrangement, with respect to the central base point selected at S32, of the target base point whose position information is acquired at S34 (S36). A method for calculating the angle may be set as appropriate. The CPU 1 of the present embodiment calculates an angle of a line segment connecting the central base point and the target base point with respect to a reference. As shown in FIG. 11, in the two-dimensional coordinates of the image coordinate system, a reference J is in the positive X direction (the rightward direction) from the central base point. The CPU 1 sets the positive X direction to 0 degrees, sets a clockwise angle from the reference, whose starting point is the central base point, to a positive angle, and sets a counterclockwise angle from the reference to a negative angle. In accordance with the position of the target base point with respect to the central base point, the CPU 1 sets the angle of the target base point as an angle from −180 degrees to 180 degrees. For example, a positive angle An4 is calculated for the base point a4, and a negative angle An3 is calculated for the base point a3. Using another method, the angle may be represented as an angle from 0 degrees to 360 degrees.

The CPU 1 determines whether the position information has been acquired by the processing at S34 for all the base points within the range selected at S33 (S37). When the processing at S34 has not been performed on some of the base points within the range selected at S33 (no at S37), the CPU 1 returns the processing to S34. When the position information has been acquired by the processing at S34 for all the base points within the range selected at S33 (yes at S37), the CPU 1 sets, as the candidate base point PK, the target base point for which the distance calculated at S35 is equal to or less than the predetermined value R. For example, the CPU 1 sets, as the candidate base point PK, each of the fourteen base points from the base point a0 to the base point a13 that are positioned on the inside of a circle C whose center is the central base point A1 shown in FIG. 5 and whose radius is R.

The CPU 1 determines whether the number of the candidate base points PK is smaller than the predetermined number 8 (S38). When the number of the candidate base points PK is smaller than 8 (yes at S38), the CPU 1 advances the processing to S50 to be described later. In this case, the sweat pore-related information is not generated for the central base point PA selected at S32. When the number of the candidate base points PK is not smaller than 8 (no at S38), the CPU 1 acquires, as the peripheral base point, the base point a2 that is the base point for which the distance calculated at S35 is smallest among the base points a0 to a13 that are the candidate base points PK selected at S38. From among the candidate base points PK, the CPU 1 acquires the base point having the N-th closest distance from the central base point PA calculated by the processing at S35 (S39). Since the base point having the closest distance from the central base point PA has already been acquired as the peripheral base point, the initial value of N is 2. When N is 2, the CPU 1 acquires, from among the base points a0 to a13, the base point a4 having the second closest distance from the central base point PA.

For each of the base points already acquired as the peripheral base points among the candidate base points PK, the CPU 1 determines, on the basis of the angle calculated at S36, whether an absolute value of an angle formed between the line segment connecting the peripheral base point and the central base point and the line segment connecting the base point acquired at S39 and the central base point is equal to or more than 15 degrees (S40). For example, when there are a plurality of the peripheral base points that have already been determined, when, for all the plurality of peripheral base points, the absolute value of the angle formed between the radial line segment connecting the central base point and the peripheral base point and the radial line segment connecting the base point newly acquired by the processing at S39 and the central base point is equal to or more than 15 degrees, the CPU 1 determines that the absolute value of the angle is equal to or more than 15 degrees. In other words, when, for even one of the already determined peripheral base points, the absolute value of the angle formed between the radial line segment connecting the central base point and the peripheral base point and the radial line segment connecting the base point newly acquired by the processing at S39 and the central base point is less than 15 degrees, the CPU 1 determines, at S40, that the absolute value of the angle is not equal to or more than 15 degrees. When N is 2 and the point a4 having the second closest distance is acquired at S39, as shown in FIG. 11, the CPU 1 determines that the absolute value of an angle An formed by the line segment connecting the base points A1 and a2 and the line segment connecting the base points A1 and a4 is equal to or more than 15 degrees (yes at S40). In this case, the CPU 1 adds the base point acquired by the processing at S39 to the peripheral base points of the central base point selected at S32 (S41), and determines whether the number of the base points already acquired as the peripheral base points is 8 (S42).

When the number of the base points is not 8 (no at S42), or when it is determined by the processing at S40 that the absolute value of the angle is not equal to or more than 15 degrees (no at S40), the CPU 1 determines whether all the base points included in the candidate base points PK have been acquired by the processing at S39 (S48). When all the base points included in the candidate base points PK have been acquired by the processing at S39 (yes at S48), the CPU 1 advances the processing to S50 to be described later. When, among the base points selected as the candidate base points PK, there is the base point that has not been acquired by the processing at S39 (no at S48), the CPU 1 increments N by one (S49) and returns the processing to the processing at S39. Through the processing at S41 that is repeatedly performed, with respect to the central base point A1, the peripheral base points a0 to a7 are added (S41), and the CPU 1 determines that the eight peripheral base points a0 to a7 have been acquired (yes at S42).

The CPU 1 sets an arrangement order of the attribute information and peripheral information of the eight peripheral base points (S43). The arrangement order indicates an arrangement order of the attribute information and the peripheral information of each of the eight peripheral base points. The peripheral information may be the position information itself of the peripheral base point or may be a calculated value that is calculated using the position information of the peripheral base point. The peripheral information may be one type of information or may be a plurality of types of information. The peripheral information of the present embodiment includes the ID of the peripheral base point acquired by the processing at S34, the angle calculated by the processing at S36, and the distance calculated by the processing at S35. Since the ID of each of the base points is associated with the position information in the list 47 and the peripheral information includes the ID, the peripheral information is associated with the position information. A method for setting the arrangement order may be determined as appropriate. The CPU 1 of the present embodiment sets, as the first peripheral base point in the arrangement order, a distant base point which is on the same ridge as the central base point PA and for which the distance from the central base point PA is farthest among the plurality of peripheral base points acquired by the processing at S39 to S42. Then, the CPU 1 sets the arrangement order of the second and subsequent peripheral base points in a predetermined direction around the central base point (a clockwise direction DS in FIG. 5, for example) from the distant base point on the basis of the arrangement on the image. With respect to the central base point A1 in FIG. 5 and FIG. 11, the arrangement order is determined sequentially from the peripheral base point a0 to the peripheral base point a7. In accordance with the arrangement order set at S43, the CPU 1 matches the arrangement order of the peripheral information with the arrangement order of the attribute information.

The CPU 1 generates radial information as part of the attribute information (S44). The radial information is information indicating, for each of the peripheral base points, whether the central base point and the peripheral base point are on the same ridge. A notation system of the radial information may be set as appropriate. In FIG. 11, when "1" indicates a case in which the central base point and the peripheral base point are on the same ridge (the radial line segments shown by the solid lines), and "0" indicates a case in which the central base point and the peripheral base point are not on the same ridge (the radial line segments shown by the alternate long and short dash lines), the radial information represented by binary numbers of the peripheral base points a0 to a7 of the central base point A1 is 1, 0, 0, 0, 1, 0, 0, 0, respectively. In the attribute information, the radial information that has a one-to-one association with the peripheral base points is represented by an eight-digit binary number that is arranged in accordance with the arrangement order determined by the processing at S43. In this case, the central base point A1 is associated with the binary number radial information 10001000. The notation system of the radial information may be changed as appropriate, such as being denoted as 0x88 in hexadecimal notation.

The CPU 1 generates surrounding information as part of the attribute information (S45). The surrounding information is information indicating, for each of the peripheral base points taken as a starting point of the surrounding line segment, whether the surrounding line segment is on the same ridge. The surrounding line segment is obtained by connecting two of the peripheral base points that are endpoints of two adjacent radial line segments, among a predetermined number of the radial line segments obtained by connecting the central base point and each of the predetermined number of peripheral base points. Which of the endpoints of the surrounding line segment is taken as the starting point may be set as appropriate. In the present embodiment, when the central base point is taken as the center, the peripheral base point that is in the counterclockwise direction, of the extending directions of the surrounding line segment, is taken as the starting point. The notation system of the surrounding information may be set as appropriate. When "1" indicates a case in which the surrounding line segment is on the same ridge in FIG. 11 (the surrounding line segments shown by the first dotted lines) and "0" indicates a case in which the surrounding line segment is not on the same ridge (the surrounding line segments shown by the second dotted lines that are finer than the first dotted lines), the surrounding information represented by binary numbers of the peripheral base points a0 to a7 of the central base point A1 is 0, 1, 1, 0, 0, 1, 1, 0, respectively. In the attribute information, the surrounding information that has the one-to-one association with the peripheral base points is represented by an eight-digit binary number that is arranged in accordance with the arrangement order determined by the processing at S43, in the same manner as the radial information. In this case, the central base point A1 is associated with the binary number surrounding information 01100110.

The notation system of the surrounding information may be changed as appropriate, such as being denoted as 0x66 in hexadecimal notation.

The CPU 1 generates the classification information as part of the attribute information (S46). For example, the CPU 1 generates the classification information on the basis of the radial information generated at S44 and the surrounding information generated at S45. More specifically, on the basis of the number of ones in the radial information generated at S44 and the number of ones in the surrounding information generated at S45, the CPU 1 generates "0x24" as the classification information of the central base point A1, for example, in the same manner as in the first embodiment.

The CPU 1 generates the sweat pore-related information with respect to the central base point PA selected by the processing at S32, and stores the generated sweat pore-related information in the RAM 3 (S47). In the case of the central base point A1, sweat pore-related information 50 is generated as shown in FIG. 12 and is stored in the RAM 3. The sweat pore-related information 50 of the base point A1 includes ID51 of the base point A1, attribute information 52 and peripheral information 53. The peripheral information includes the ID, the angle and the distance for each of the peripheral base points. In the list 47 in FIG. 9, the ID is associated with the position information. The attribute information and the peripheral information are arranged in accordance with the arrangement order set at S43. In the attribute information, the classification information that does not have the one-to-one association with the peripheral base points does not have the arrangement in accordance with the arrangement order.

The CPU 1 determines whether or not all the base points determined by the processing at S23 have been selected as the central base point by the processing at S32 (S50). When there is the base point that has not been selected (no at S50), the CPU 1 returns the processing to S32. When all the base points have been selected as the central base point (yes at S50), the CPU 1 ends the sweat pore-related information generation processing and returns the processing to the image analysis processing shown in FIG. 8. After the processing at S25, the CPU 1 stores the sweat pore-related information generated by the processing at S47 in the RAM 3 as the authentication information (S28). The CPU 1 ends the image analysis processing and returns the processing to the authentication information processing shown in FIG. 7. Through the image analysis processing, the sweat pore-related information is generated with respect to a plurality of the base points including the base points A1 to A10 shown in FIG. 13. As shown in FIG. 14, the CPU 1 generates and stores authentication information 70 that includes the sweat pore-related information 50 relating to each of the plurality of base points.

After the processing at S11, the CPU 1 determines whether the authentication information including the sweat pore-related information has been acquired at S11 (S12). When the authentication information has not been acquired (no at S12), the CPU 1 performs error notification (S16). For example, the CPU 1 displays an error message on the display portion 6. When the authentication information has been acquired (yes at S12), the CPU 1 determines whether to register the authentication information acquired at S11 in the DB 28 (refer to FIG. 2) as the registration authentication information (S13). The information indicating whether to register the authentication information is included in the start command, for example. In a specific example, it is determined that the authentication information is to be registered (yes at S13), and the CPU 1 stores the authentication information acquired at S11 in the DB 28 of the flash memory 4 (S14). When the authentication information is not to be registered (no at S13), the CPU 1 performs collation processing in which the authentication information acquired at S11 is used as the collation authentication information that is a collation target (S15). After S14, S15 or S16, the CPU 1 ends the authentication information processing.

2. Processing at Time of Collation

Figure 13:
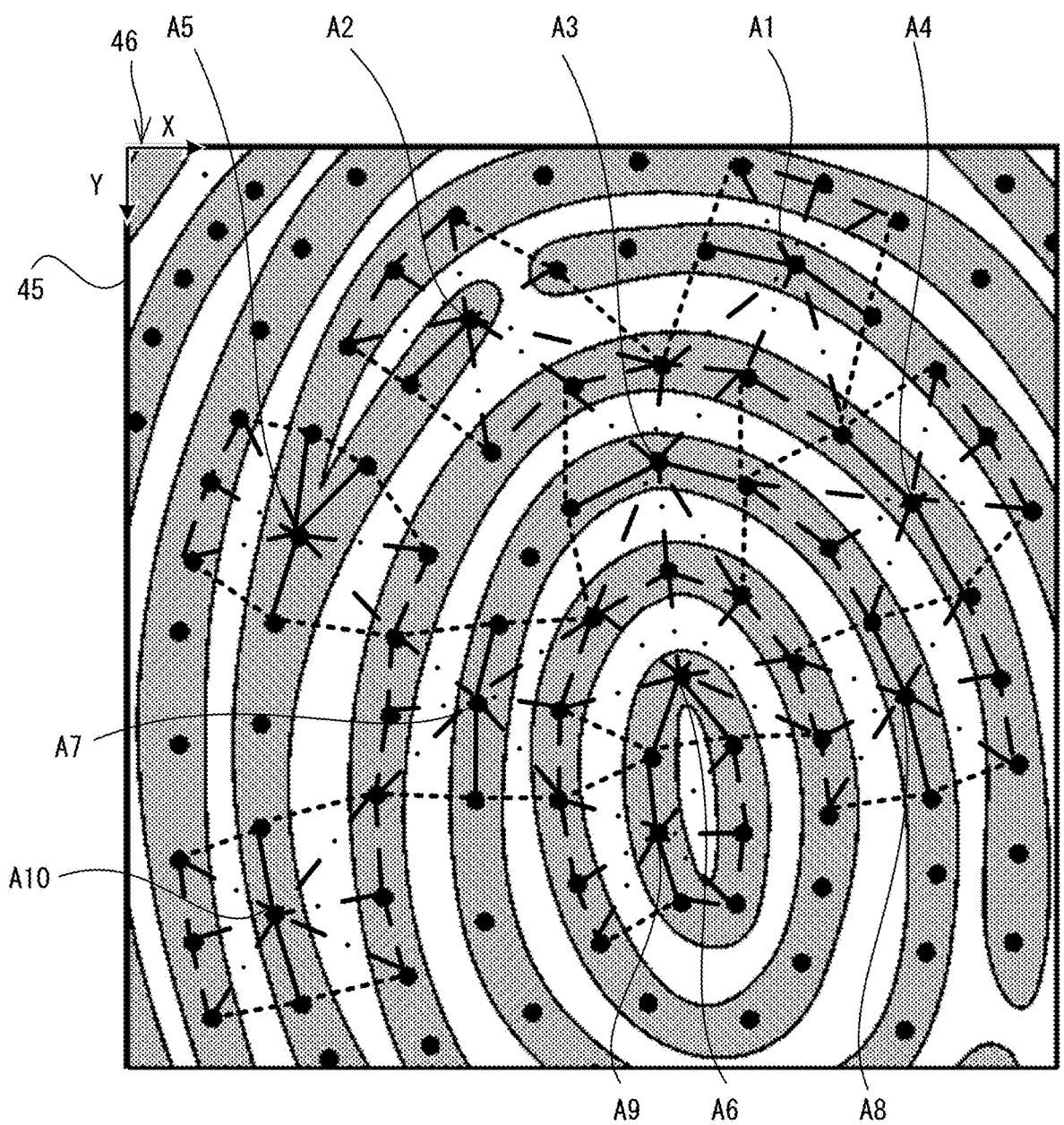
FIG. 13 is an explanatory diagram of the sweat pore-related information acquired for each of the plurality of base points on the basis of the image.
Figure 14:
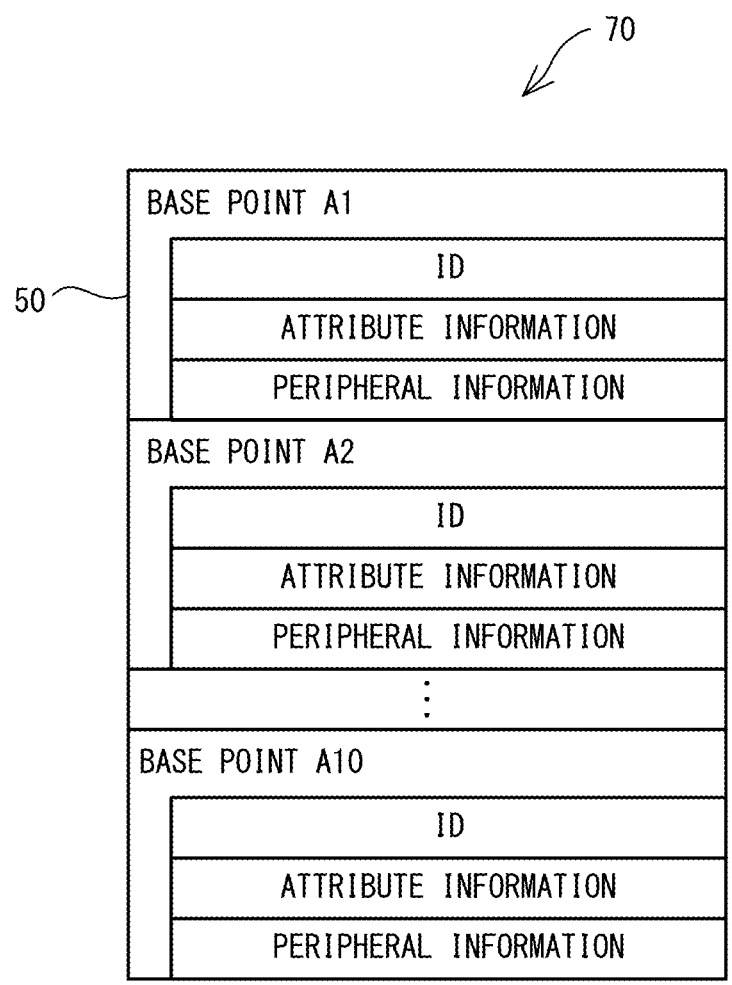
FIG. 14 is an explanatory diagram of authentication information including the sweat pore-related information acquired for each of the plurality of base points on the basis of the image.
Figure 15:
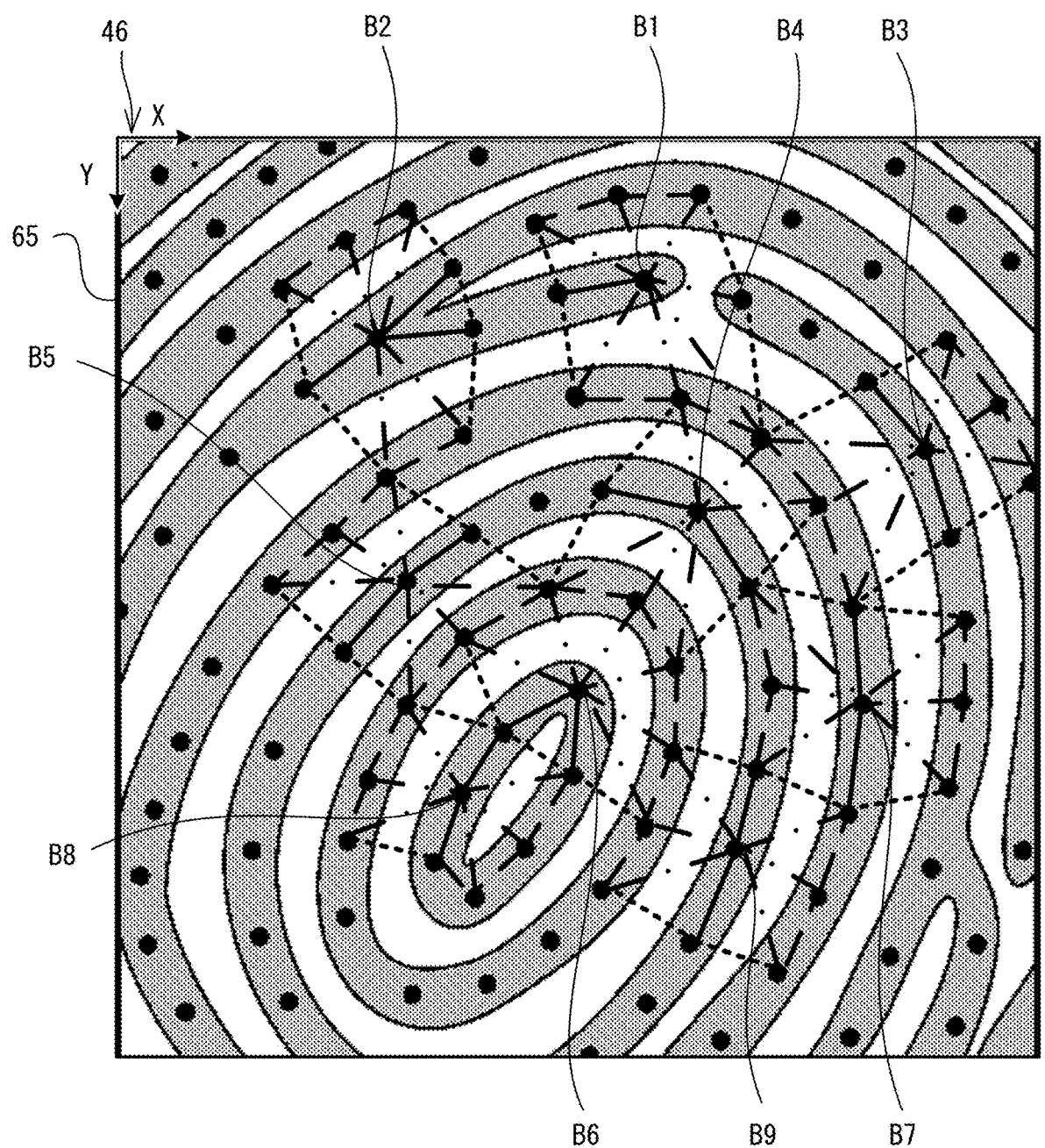
FIG. 15 is an explanatory diagram of the sweat pore-related information acquired for each of the plurality of base points on the basis of the image.

A case will be explained in which the authentication information including the sweat pore-related information about a plurality of the central base points including the central base points A1 to A10 extracted from the image 45 in FIG. 13 is used as the registration authentication information, and the authentication information including the sweat pore-related information about a plurality of the base points including central base points B1 to B9 is generated from an image 65 in FIG. 15 as a collation image that is a collation target. In the authentication information processing at the time of collation, the processing at S11 is performed in the same manner as in the authentication information processing at the time of registration. Through the processing at S11, the authentication information including the sweat pore-related information about the plurality of base points including the central base points B1 to B9 is generated from the image 65.

At S12 of the authentication information processing in FIG. 7, it is determined that the authentication information has been acquired (yes at S12), and it is determined that the authentication information is not to be registered on the basis of the start command (no at S13). The CPU 1 performs the collation processing (S15). In the collation processing, the CPU 1 compares a collation base point (the base point for collation) and a registration base point (the base point for registration) for which it is determined that the respective attribute information match each other, and determines a correspondence between the collation authentication information and the registration authentication information used to calculate a degree of similarity. Thus, the degree of similarity of the authentication information is calculated.

Figure 16:
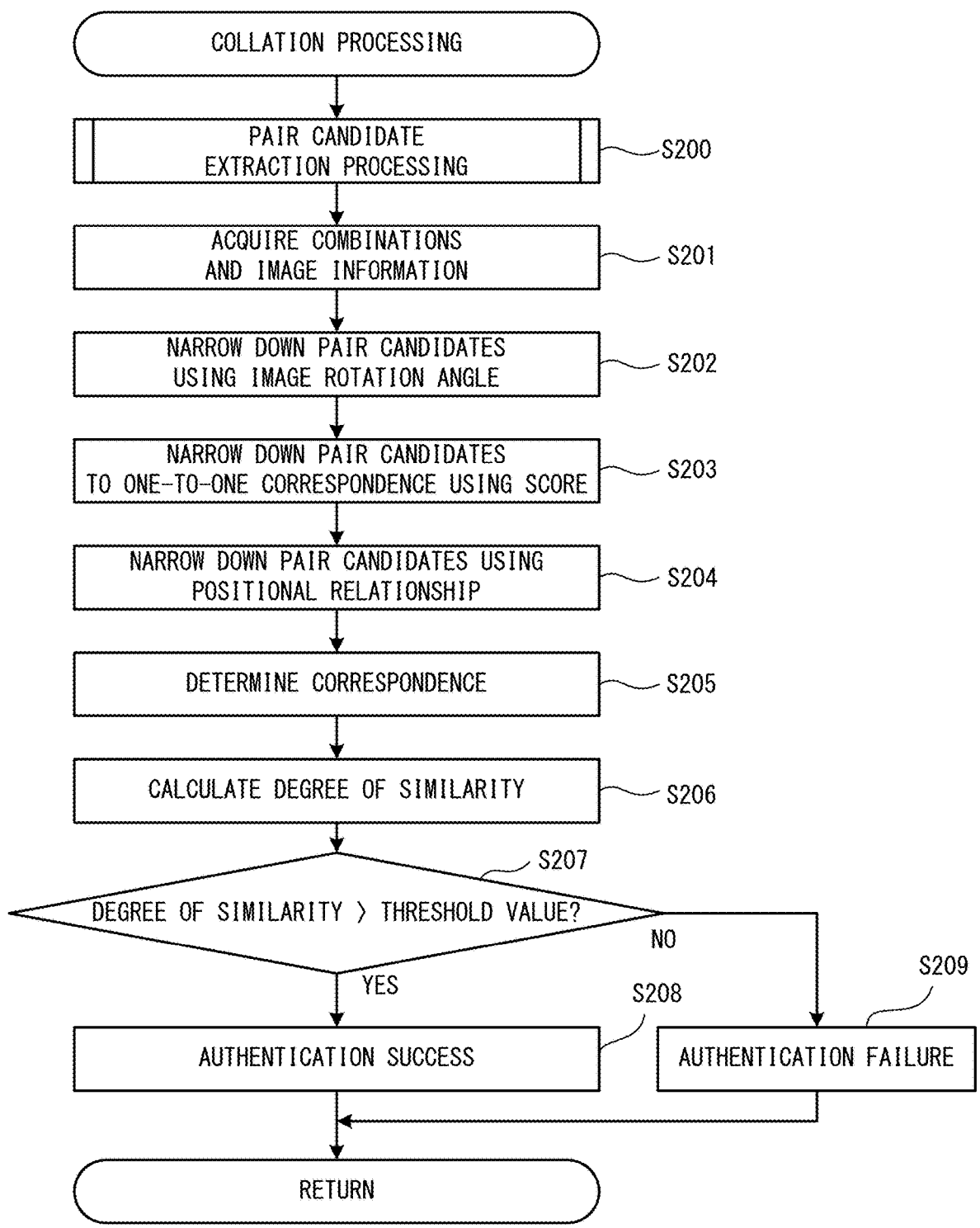
FIG. 16 is a flowchart of collation processing that is performed in the authentication information processing shown in FIG. 7.

As shown in FIG. 16, in the collation processing, the CPU 1 performs pair candidate extraction processing (S200). In the pair candidate extraction processing, from among the collation authentication information generated by the processing at S11 and the registration authentication information stored in the DB 28, the CPU 1 extracts, as a pair candidate that is a target to compare the correspondence between the collation authentication information and the registration authentication information, a pair of the collation base point (the sweat pore-related information) and the registration base point (the sweat pore-related information) for which the respective attribute information associated with the base points match each other. On the basis of the sweat pore-related information, the CPU 1 calculates a score of the pair candidate.

Figure 17:
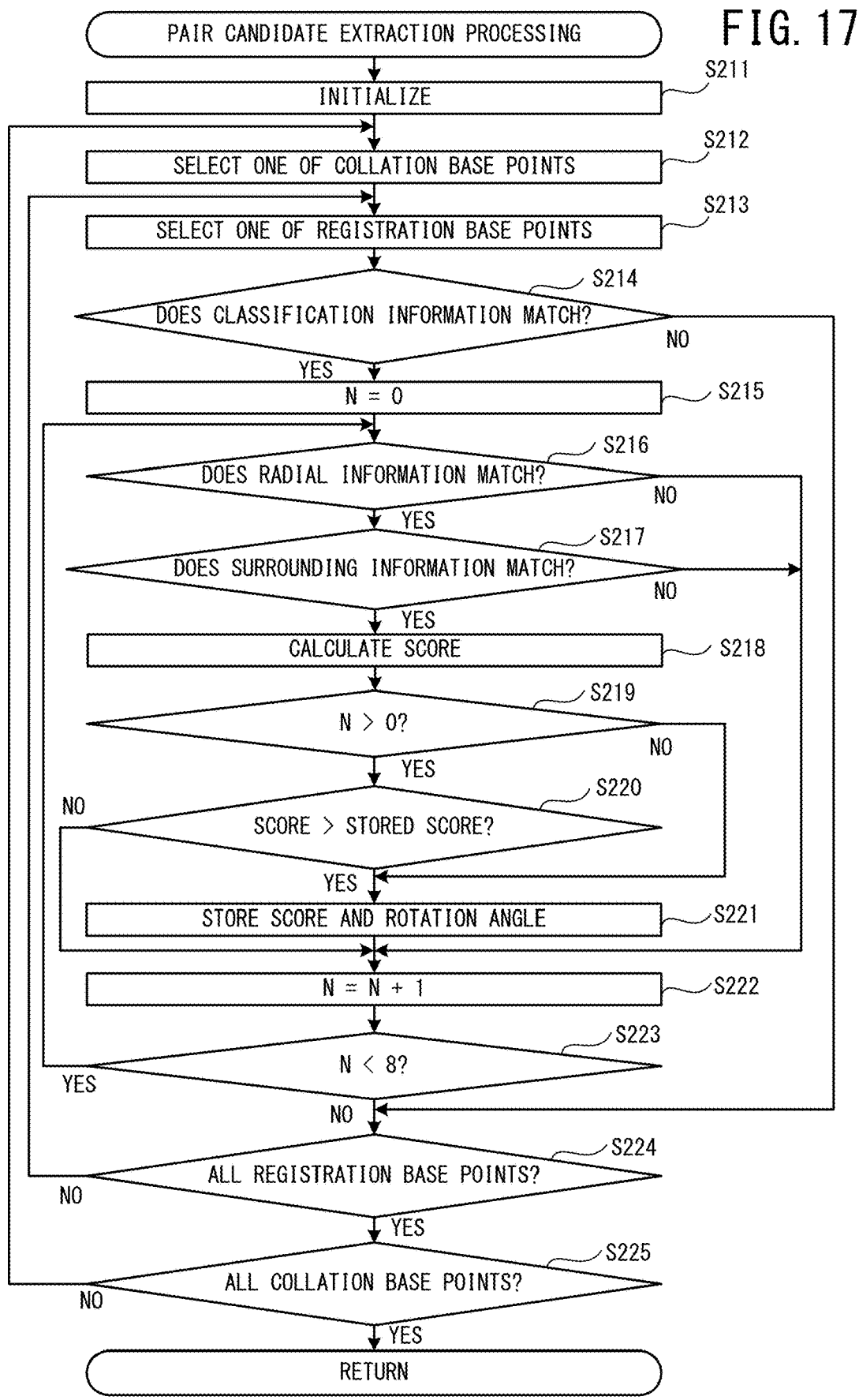
FIG. 17 is a flowchart of pair candidate extraction processing that is performed in the collation processing shown in FIG. 16.
Figure 18:
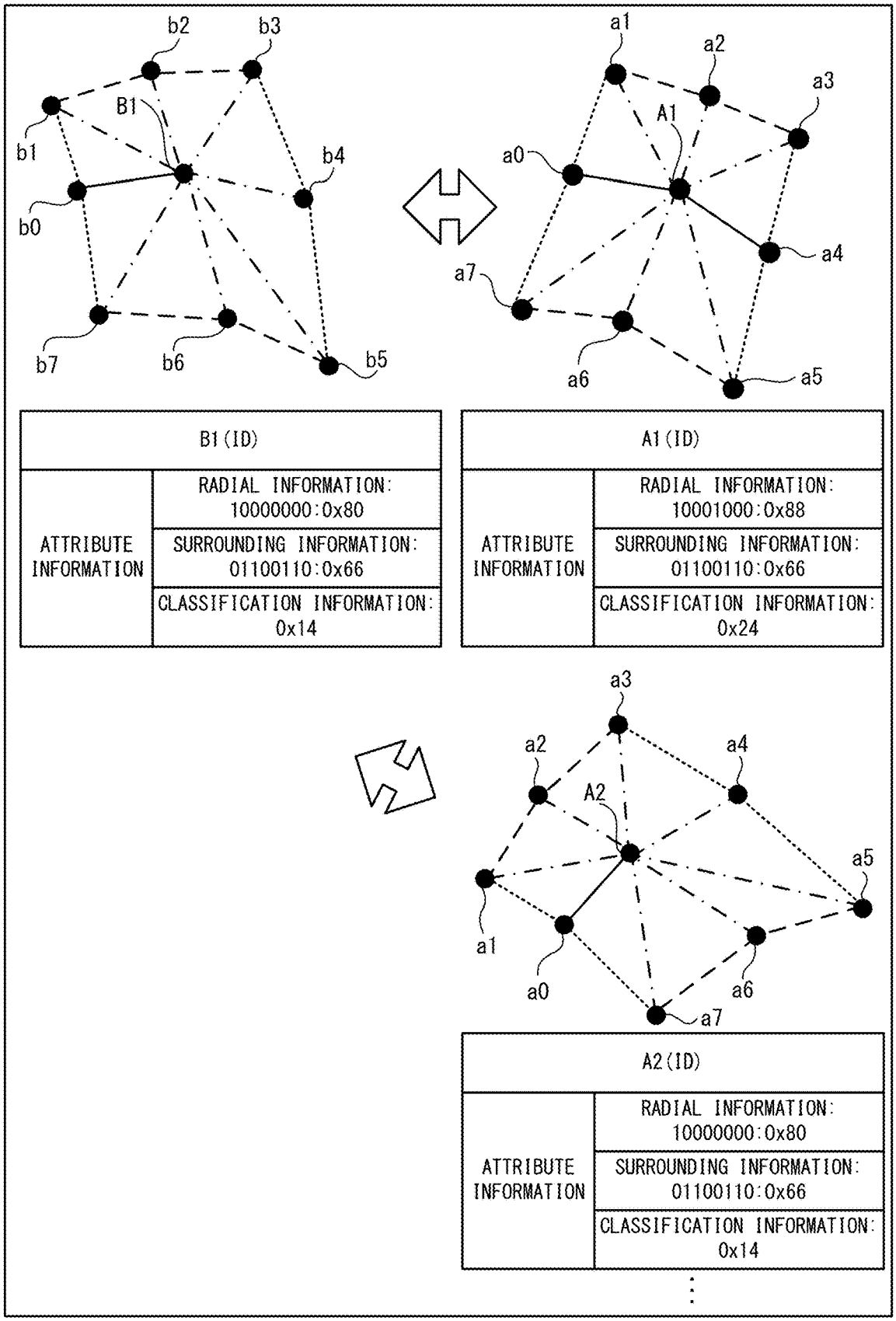
FIG. 18 is an explanatory diagram of processing that compares attribute information of collation base points with attribute information of registration base points.

As shown in FIG. 17, in the pair candidate extraction processing, the CPU 1 initializes a list stored in the RAM 3 to extract the pair candidates (S211). The CPU 1 selects one of the base points (the central base points) that have not been selected at S212, from among the base points for which the sweat pore-related information included in the collation authentication information generated by the processing at S11 has been generated (S212). For example, the CPU 1 selects the base point B1 from among the base points for which the sweat pore-related information included in the collation authentication information has been generated. The CPU 1 selects one of the base points (the central base points) that have not been selected by the processing at S213, from among the base points for which the sweat pore-related information included in the registration authentication information registered in the DB 28 has been generated (S213). For example, the CPU 1 selects the base point A1 from among the base points for which the sweat pore-related information included in the registration authentication information has been generated. The CPU 1 determines whether the classification information included in the associated attribute information is a match between the collation base point selected by the processing at S212 and the registration base point selected by the processing at S213 (S214). As shown in FIG. 18, the classification information of the base point B1 is 0x14 and the classification information of the base point A1 is 0x24, and they are different from each other (no at S214). In this case, the CPU 1 does not extract, as the pair candidate, a combination of the base point B1 selected at S212 and the base point A1 selected at S213, and determines whether all the registration base points have been selected by the processing at S213 (S224). When there is the registration base point that has not been selected (no at S224), the CPU 1 returns the processing to S213.

Figure 19:
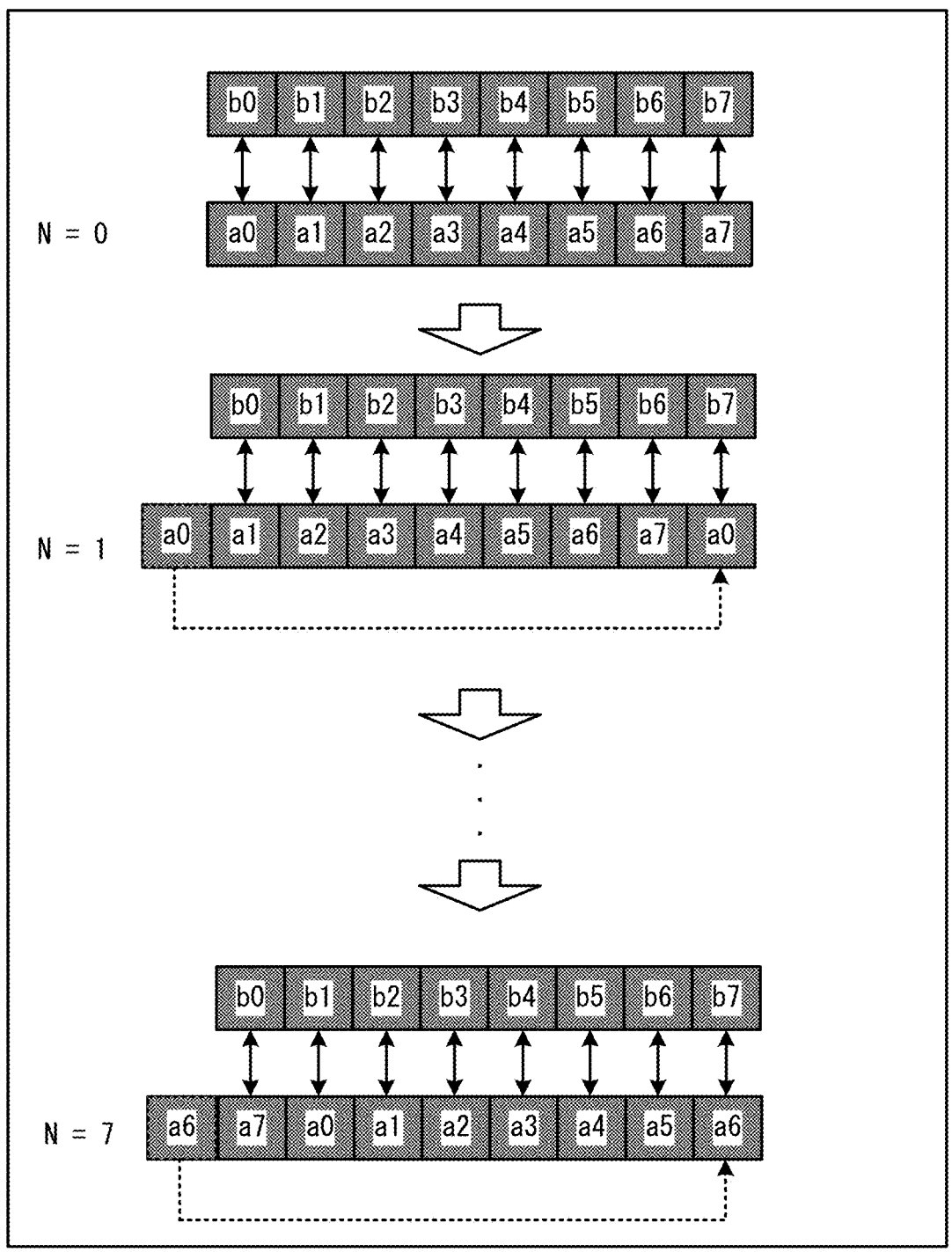
FIG. 19 is an explanatory diagram of processing that performs comparison while taking contraction and rotation of the image into consideration, for each of the attribute information and peripheral information having a one-to-one association with the peripheral base points.

When the registration base point A2 is selected (S213), as shown in FIG. 18, the classification information of the base point B1 is 0x14 and the classification information of the base point A2 is 0x14, and they match each other (yes at S214). In this case, the CPU 1 sets a variable N to 0 (S215). The variable N is a variable to sequentially compare the attribute information (the radial information and the surrounding information in the present embodiment) that have a one-to-one association with the peripheral base points, while taking the contraction and rotation of the image into consideration. The CPU 1 determines whether the radial information included in the associated attribute information is a match between the collation base point selected by the processing at S212 and the registration base point selected by the processing at S213 (S216). The CPU 1 compares the radial information of the collation base points and the radial information of the registration base points corresponding to the variable N. As shown in FIG. 19, when the variable N is 0 with respect to the base point A2, the radial information corresponding to peripheral base points b0 to b7 is compared with the radial information corresponding to the peripheral base points a0 to a7, respectively. When the variable N is 1, the radial information corresponding to the peripheral base points b0 to b7 is compared with the radial information corresponding to the peripheral base points a1 to a7 and a0, respectively. In other words, the CPU 1 changes a reference start position of the attribute information of the registration base point in accordance with the variable N. A collation base point bm (m is an integer from 0 to 7) is compared with a registration base point a (MOD (N+m, 8)). MOD (N+m, 8) is the remainder when dividing the sum of N and m by 8. By doing this, for example, when the variable N is 1, the CPU 1 can compare the radial information (the attribute information), assuming a case in which the arrangement order is shifted in the clockwise direction from the peripheral base point a1 that is after the peripheral base point a0 in the arrangement order. In other words, while taking the contraction and rotation of the image into consideration, the CPU 1 can sequentially compare the attribute information (the radial information and the surrounding information in the present embodiment) that has the one-to-one association with the peripheral base points.

When the radial information does not match (no at S216), the CPU 1 advances the processing to S222 to be described later. The radial information of the base point B1 is 10000000, and matches the radial information 10000000 of the base point A2 when the variable N is 0 (yes at S216). In this case, the CPU 1 determines whether the surrounding information included in the associated attribute information is a match between the collation base point selected by the processing at S212 and the registration base point selected by the processing at S213 (S217). In the same manner as in the processing at S216, in the processing at S217, the CPU 1 compares the surrounding information of the collation base points and the surrounding information of the registration base points corresponding to the variable N.

Figure 20:
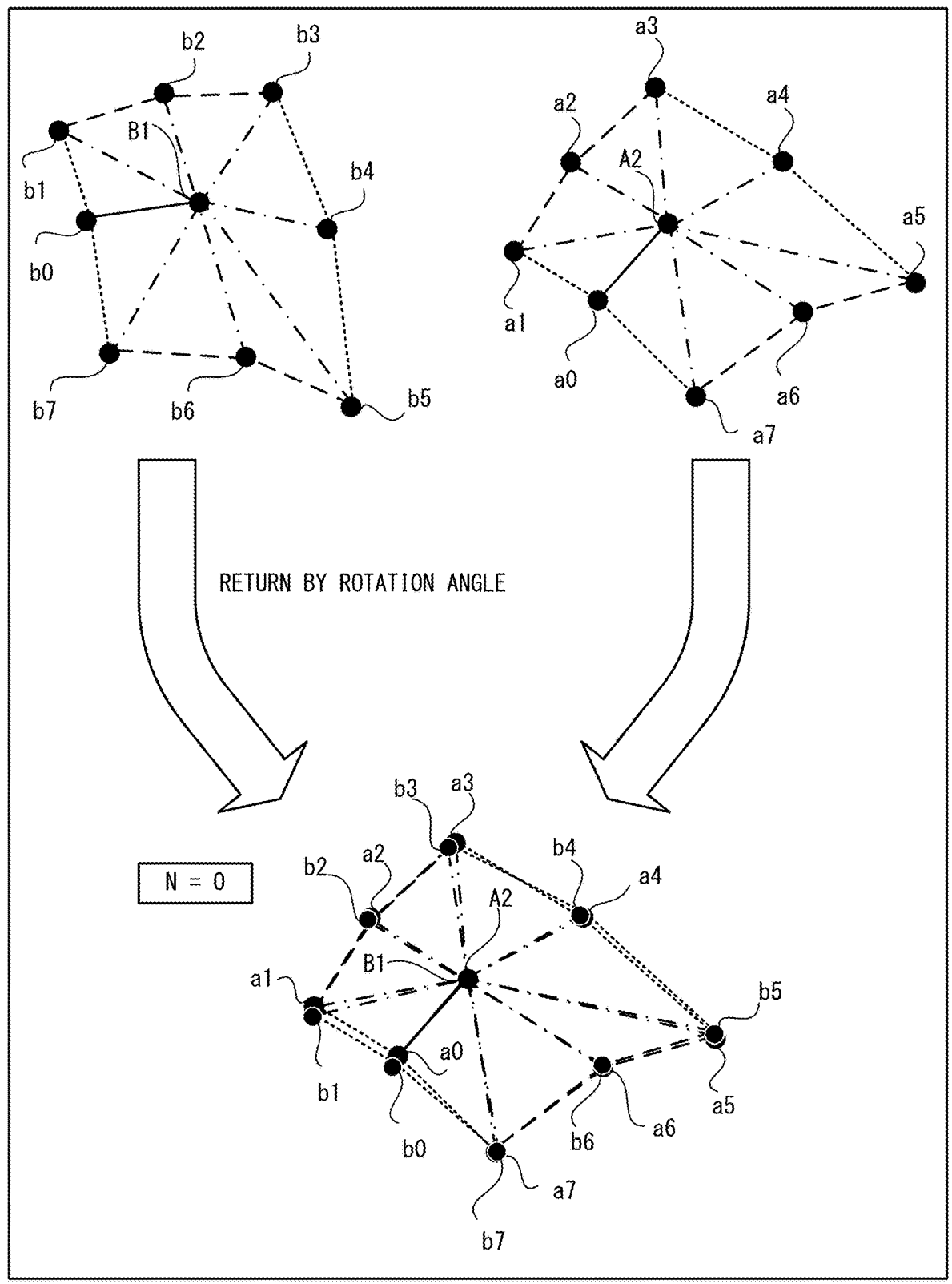
FIG. 20 is an explanatory diagram of a process that calculates a score for the collation base points and the registration base points extracted as pair candidates.

When the surrounding information does not match (no at S217), the CPU 1 advances the processing to S222 to be described later. The surrounding information of the base point B1 is 01100110, and matches the surrounding information 01100110 of the base point A2 when the variable N is 0 (yes at S217). In this case, the CPU 1 calculates, from the peripheral information included in the sweat pore-related information, a score indicating the degree of similarity between the collation base point selected by the processing at S212 and the registration base point corresponding to the variable N selected by the processing at S213 (S218). The peripheral information included in the sweat pore-related information of the present embodiment includes the ID associated with the position information, the angle and the distance. For example, the CPU 1 of the present embodiment calculates the score using an angle comparison amount and a distance comparison amount of eight sets of the peripheral base points for which the comparison between the registration base points and the collation base points is currently being performed. When the variable N is 0, as shown in FIG. 20, the score indicates a displacement amount of the angle and the distance of the eight sets of peripheral base points when the central base point is a match between the registration base point A2 and the collation base point B1 and the arrangements of the eight sets of peripheral base points are compared in a state in which one set of the radial line segments, which are taken as a reference based on N, are overlapped while taking a rotation angle into consideration. The one set of radial line segments taken as the reference based on N is a combination of the radial line segments whose endpoints are the collation base point b0 and the registration base point a (MOD (N, 8)). The eight sets of peripheral base points are the base points of the combinations indicated by two-way arrows in FIG. 19, and are the combinations of the collation base point bm and the registration base point a (MOD (N+m, 8)), where m is an integer from 0 to 7. The rotation angle indicates at what angle the collation image is assumed to be rotated with respect to a registration image, and is an angle that is calculated on the basis of the sweat pore-related information. The rotation angle of the present embodiment is defined whereby the angle in the clockwise direction in the image coordinate system is a positive angle. The comparison amount is a value that is calculated by comparing the peripheral information included in the sweat pore-related information between the collation base point and the registration base point.

When the angle of the collation base point bm is defined as an angle Bnm and the angle of the registration base point a (MOD (N+m, 8)) is defined as an angle An (MOD (N+m, 8)), the angle comparison amount of eight sets of angles may be expressed as a sum of squares of a difference in the rotation angle calculated by Equation (1), where m is an integer from 0 to 7.

Difference in rotation angle=$Bnm-An(MOD(N+m, 8))+AnN-Bn0$     Equation (1)

When the distance of the collation base point bm is defined as a distance Dbm and the distance of the registration base point a (MOD (N+m, 8)) is defined as a distance Da (MOD (N+m, 8)), the distance comparison amount of eight sets of distances may be expressed as a sum of ratios of differences in the distance calculated by Equation (2), where m is an integer from 0 to 7.

Ratio of differences in distance=$|Dbm-Da(MOD(N+m,8))|/min(Dbm, Da(MOD(N+m,8)))$     Equation (2)

Note that min (Dbm, Da (MOD (N+m, 8))) is the smaller value, of Dbm and Da (MOD (N+m, 8)). If it is assumed that the score (a score maximum value) is 100 when the angle comparison amount and the distance comparison amount are 0, the score of the collation base point B1 and the registration base point A2 is calculated as 85, for example, on the basis of Equation (3), and is registered in the list.

Score=$(\text{comparison amount maximum value}-(\text{distance comparison amount}\times\text{constant}+\text{angle comparison amount}))/\text{comparison amount maximum value}\times\text{score maximum value}$     Equation (3)

In Equation (3), the constant is a value that is appropriately set in order to adjust the distance comparison amount with respect to the angle comparison amount, and is 100, for example. The comparison amount maximum value is an allowable maximum value of a sum of the angle comparison amount and a value obtained by multiplying the distance comparison amount by the constant. When the sum of the angle comparison amount and the value obtained by multiplying the distance comparison amount by the constant is larger than the comparison amount maximum value, in Equation (3), the comparison amount maximum value is set as the sum of the angle comparison amount and the value obtained by multiplying the distance comparison amount by the constant. The score maximum value is a maximum value of the score that can be obtained, and is 100, for example. The rotation angle between the collation base point B1 and the registration base point A2 is calculated as 41 degrees and is stored in the list.

The CPU 1 determines whether N is larger than 0 (S219). When N is larger than 0 (yes at S219), the CPU 1 determines whether the score calculated by the processing at S218 is larger than the score stored in the list (S220). When N is not larger than 0 (no at S219) or is larger than the stored score (yes at S220), the CPU 1 stores the score calculated at S218 and the rotation angle in the list of the RAM 3 (S221). By performing this processing, the value for which the attribute information is a match between the collation base point and the registration base point, and for which the score is largest is stored in the list.

When the score calculated by the processing at S218 is not larger than the stored score (no at S220), or after S221, the CPU 1 increments the variable N by 1 (S222). The CPU 1 determines whether N is smaller than 8 (S223). The threshold value 8 at S223 is the same as the number of the peripheral base points, and is set in order to compare the attribute information for all the combinations while taking an influence of the rotation of the image into consideration. When N is smaller than 8 (yes at S223), the CPU 1 returns the processing to S216. When N is not smaller than 8 (no at S223), the CPU 1 determines whether all the registration base points included in the authentication information stored in the DB 28 have been selected by the processing at S213 (S224). When there is the registration base point that has not been selected (no at S224), the CPU 1 returns the processing to S213. When all the registration base points have been selected by the processing at S213 (yes at S224), the CPU 1 determines whether all the collation base points included in the collation authentication information have been selected by the processing at S212 (S225).

When there is the collation base point that has not been selected (no at S225), the CPU 1 returns the processing to S212. When all the collation base points have been selected by the processing at S212 (yes at S225), the CPU 1 ends the pair candidate extraction processing and returns the processing to the collation processing in FIG. 16. By performing the pair candidate extraction processing, as shown in FIG. 21, the score and the rotation angle are acquired for each of the registration base points (the sweat pore-related information) and the collation base points (the sweat pore-related information) extracted as the pair candidates. In FIG. 21, the value on the upper side of each of the combinations of the registration base points and the collation base points indicates the score, and the value on the lower side indicates the rotation angle. Combinations in which columns of the score and the rotation angle are blank are combinations that are not extracted as the pair candidates, and are combinations in which the attribute information does not match. At this stage, combinations in which a plurality of the registration base points (the sweat pore-related information) are extracted as the pair candidates with respect to the single collation base point (the sweat pore-related information) are included. For example, with respect to the collation base point B3, the registration base points A1, A3, A4, A7, A8 and A10 are extracted as the pair candidates. In a specific example, thirty-six sets of combinations are extracted as the pair candidates, from among ninety sets of combinations of the ten registration base points and the nine collation base points (the sweat pore-related information).

After S200, with respect to the pair candidates extracted by the processing at S200, the CPU 1 compares the peripheral information included in the sweat pore-related information for collation and the peripheral information included in the sweat pore-related information for registration, and determines a correspondence between skin information for collation and skin information for registration. Specifically, the CPU 1 acquires combinations (pairs, correspondences) of the sweat pore-related information for collation and the sweat pore-related information for registration that are extracted as the pair candidates, and a plurality of pieces of image information including at least one selected from the group of a rotation amount and a movement amount between the collation image and the registration image, which are calculated from the sweat pore-related information for collation and the sweat pore-related information for registration (S201). The image information of the present embodiment is stored by the processing at S221, and is the rotation angle indicating the rotation amount between the collation image and the registration image. The CPU 1 acquires the combinations of the pair candidates and the rotation angles shown in FIG. 21. The CPU 1 compares the pieces of image information of the acquired plurality of sets of combinations of the sweat pore-related information for collation and the sweat pore-related information for registration, and narrows down the pair candidates (S202). The CPU 1 narrows down the pair candidates such that the image information thereof falls within a predetermined range that is set on the basis of a representative value of the image information of the acquired plurality of sets of pair candidates. It is sufficient that the representative value be a value that represents a feature of the plurality of pieces of image information, and may be, for example, an average value, a mode value, a median value or the like of the pieces of image information.

Figure 22:
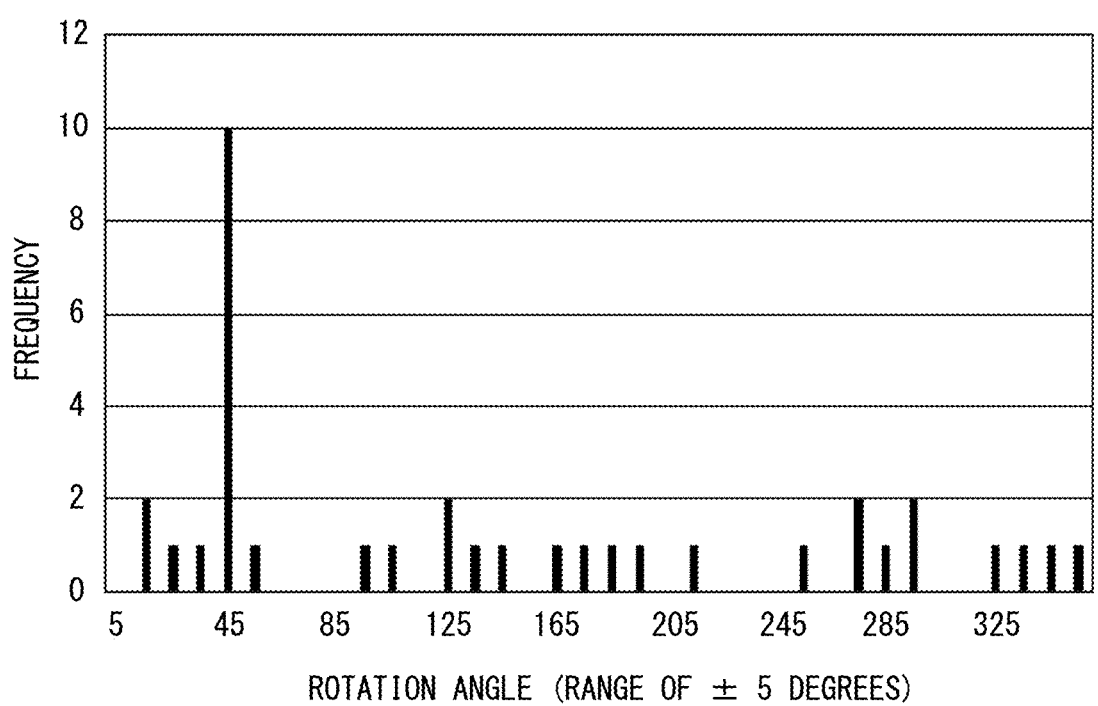
FIG. 22 is a histogram obtained by classifying the rotation angles of the pair candidates into angles within a predetermined range, and is an explanatory diagram of processing that narrows down the pair candidates using the rotation angles.

The CPU 1 of the present embodiment classifies the rotation angles of the pair candidates into angles within a predetermined range, and extracts the pair candidates having the rotation angle that corresponds to a plus/minus predetermined angle from a representative value of a range of the rotation angle that appears most frequently, thus narrowing down the pair candidates. It is preferable that the predetermined range be a range that is equal to or more than 1 degree (a 360 resolution) and equal to or less than 20 degrees (an 18 resolution). The predetermined angle is determined as appropriate while taking the predetermined range into consideration. It is preferable that the predetermined angle be an angle that includes at least three resolutions and that is equal to or more than plus/minus 15 degrees from the representative value and equal to or less than 60 degrees. In a specific example, as shown in FIG. 22, for example, the CPU 1 classifies the rotation angles of the pair candidates into angles within each of 10-degree ranges (for example, a range whose representative value is expressed as 5 degrees and which is equal to or more than 0 degrees and less than 10 degrees, a range whose representative value is expressed as 15 degrees and which is equal to or more than 10 degrees and less than 20 degrees, or the like). In this case, as shown in FIG. 22, the range whose representative value is expressed as 45 degrees has the largest frequency. The CPU 1 takes the representative value of the range having the largest frequency as the representative value of the image information, and extracts the pair candidates for which the rotation angle falls within a range from 30 degrees to 60 degrees that is within plus/minus 15 degrees from the representative value 45 degrees. For example, in the combination of A1 and B3, the rotation angle is 44 degrees and is a value within the range from 30 degrees to 60 degrees. Therefore, this combination of A1 and B3 is extracted by the processing at S202. In the combination of A1 and B4, the rotation angle is 290 degrees and is not a value within the range from 30 degrees to 60 degrees. Therefore, this combination of A1 and B4 is not extracted by the processing at S202. The combinations indicated by dot hatching in FIG. 21 that include the combination of A1 and B4 are combinations that have not been extracted by the processing at S202. In the processing at S202, when the rotation angles of the pair candidates are classified into angles within the predetermined range, the CPU 1 may take a moving average of the frequency, taking account of the possibility that the distribution may vary, and may identify the range having the largest frequency.

When the collation base point and the registration base point do not have a one-to-one correspondence, the CPU 1 extracts the pair candidate having the largest score from among the pair candidates narrowed down by the processing at S202, and narrows down the pair candidates so that the collation base point and the registration base point have the one-to-one correspondence (S203). The CPU 1 of the present embodiment narrows down the pair candidates shown in FIG. 21 to the pair candidates indicated by oblique hatching.

Figure 23:
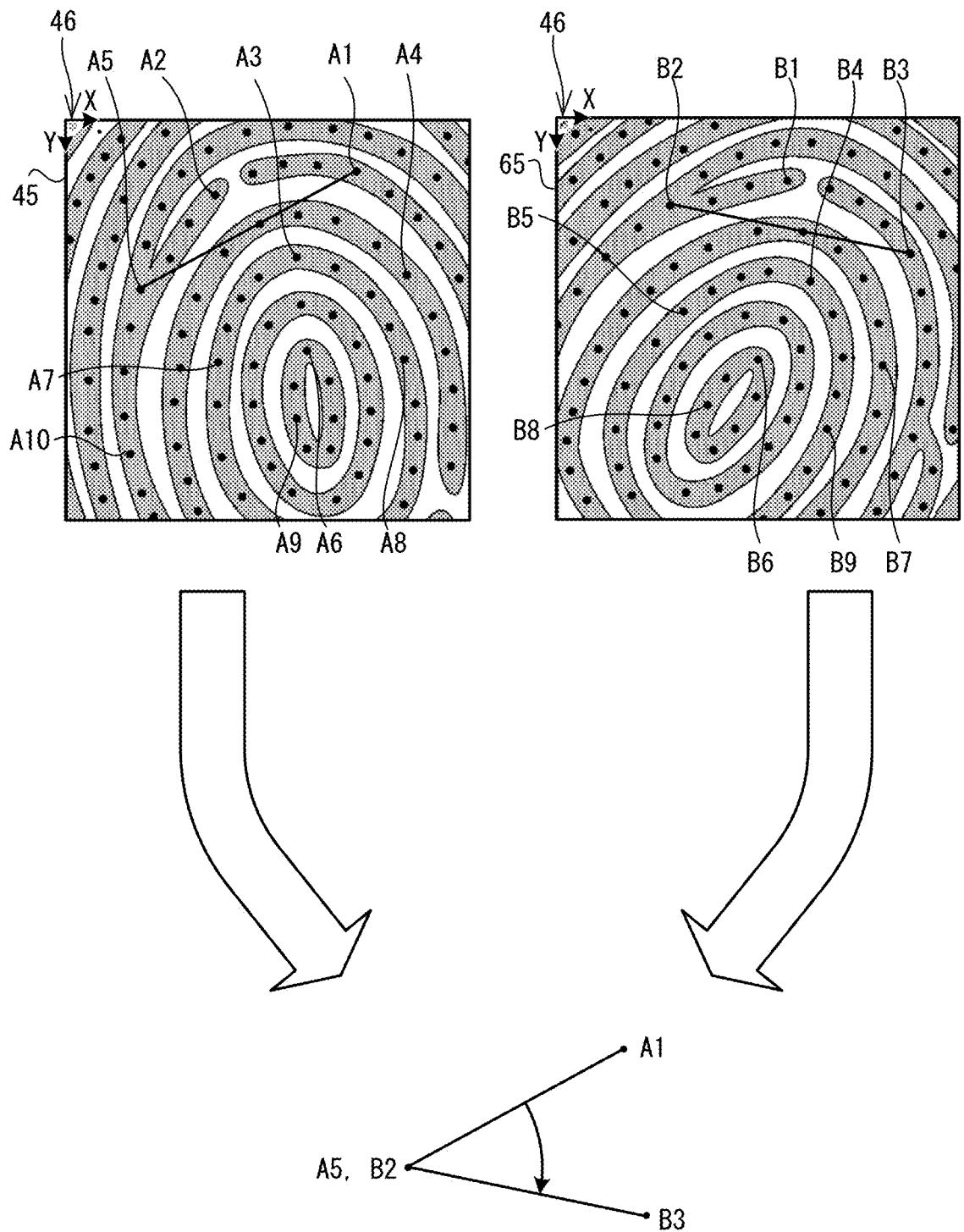
FIG. 23 is an explanatory diagram of processing that narrows down the pair candidates using a positional relationship between two sets of the pair candidates.

From among the pair candidates narrowed down by the processing at S202 and S203, the CPU 1 further narrows down the pair candidates by comparing at least one selected from the group of lengths and angles of line segments connecting each of the central base points of a plurality of sets of the pair candidates that are arbitrarily selected (S204). Conditions for selecting the plurality of sets of pair candidates may be changed as appropriate. The CPU 1 of the present embodiment selects any two sets of pair candidates from among the pair candidates narrowed down by the processing at S203, and further narrows down the pair candidates using a positional relationship between the line segments connecting the base points of the selected two sets of pair candidates. Specifically, the CPU 1 further narrows down the pair candidates by extracting a case in which the angle of the line segments connecting the base points of the selected two sets of pair candidates, and the lengths of the line segments each satisfy a predetermined condition. For example, as shown in FIG. 23, when the base points A5 and B2, and the base points A1 and B3 are selected as the two sets of pair candidates, with respect to the line segment connecting the base points A5 and A1 and the line segment connecting the base points B2 and B3, it is determined whether the angle relating to the two line segments and the lengths of the line segments each satisfy the predetermined condition. The condition relating to the angle is a condition that a difference between the angle of the line segment connecting the base points A5 and A1 and the angle of the line segment connecting the base points B2 and B3 falls within a predetermined range. The predetermined range is, for example, a range of plus/minus 5 degrees of a representative value of the angle. The representative value is, for example, an average value of the rotation angles of the pair candidates narrowed down by the processing at S203. In the present embodiment, the predetermined range at S204 is narrower than the range at S202. The condition relating to the length is a condition that a length d1 of the line segment connecting the base points A5 and A1 and a length d2 of the line segment connecting the base points B2 and B3 satisfy Equation (4). At S204, the CPU 1 narrows down the pair candidates on the basis of the condition relating to the angle and the condition relating to the length. The CPU 1 of the present embodiment selects the two sets of pair candidates, compares the lengths and the angles of the line segments connecting each of the central base points of the pair candidates, and repeats the processing of narrowing down the pair candidates until predetermined conditions are satisfied. The predetermined conditions are, for example, conditions that the pair candidates of all the combinations narrowed down by the processing at S202 and S203 are selected and it is determined whether the condition relating to the angle and the condition relating to the length are satisfied.

$$|d1-d2|\times2/(d1+d2)<0.1 \qquad \text{Equation (4)}$$

The CPU 1 determines, as pairs, the pair candidates narrowed down by the processing at S202 to S204 (S205). In addition to the processing at S202 to S204, the CPU 1 may narrow down the pair candidates using another condition and thus may determine the pairs. The CPU 1 calculates the degree of similarity between the collation authentication information and the registration authentication information using a correspondence between the collation authentication information (the base points) and the registration authentication information (the base points) narrowed down by the processing at S202 to S204 and determined as the pairs by the processing at S205 (S206). The CPU 1 of the present embodiment calculates a score SC using a sum of the scores of the pairs determined at S205. For example, the CPU 1 uses, as the score SC, the sum of the scores of the pairs determined at S205. The CPU 1 may calculate the score SC by substituting a sum of the degrees of similarity into a predetermined formula. For example, as the value of the score SC increases, the score SC indicates that the collation authentication information and the registration authentication information are more similar to each other, in comparison to when the value is smaller The CPU 1 determines whether the degree of similarity (the score SC) calculated at S206 is larger than a threshold value (S207). When the degree of similarity is larger than the threshold value (yes at S207), the CPU 1 sets "success" as an authentication result of the skin authentication (S208). When the degree of similarity is not larger than the threshold value (no at S207), the CPU 1 sets "failure" as the authentication result of the skin authentication (S209). In the processing at S208 and S209, the CPU 1 may perform notification, such as displaying the authentication result on the display portion 6, as necessary. The CPU 1 ends the collation processing and returns the processing to the authentication information processing in FIG. 7. After S15 in FIG. 7, the CPU 1 ends the authentication information processing.

First Evaluation Test

Figure 24:
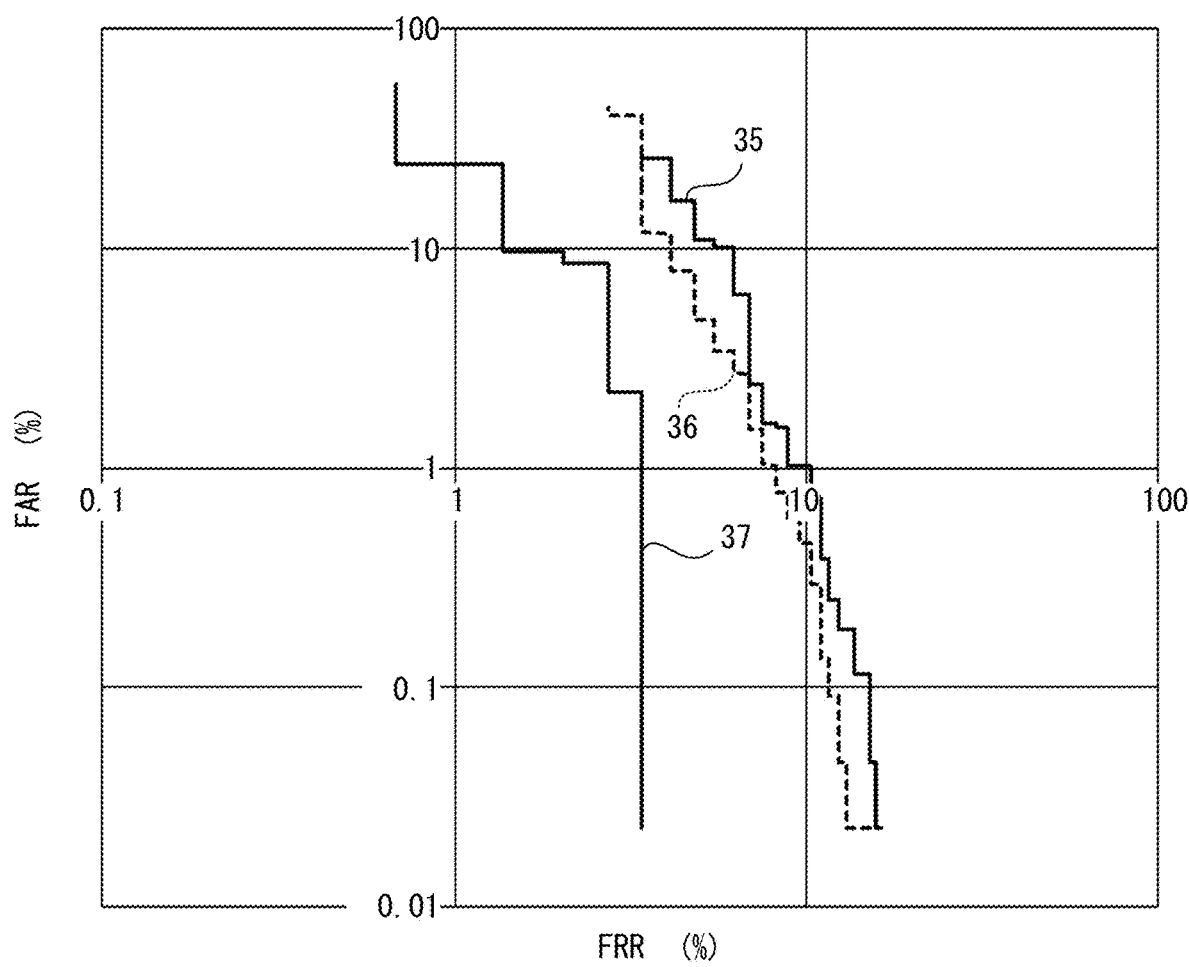
FIG. 24 is a graph showing results of a first evaluation test.

An evaluation test was conducted to verify whether authentication performance is improved by using the sweat pore-related information for the collation. For each of Conditions 1 to 3 to be described below, an optical touch sensor was used to acquire 5 to 10 images per finger for 31 fingers, each being an image of 2000 dpi having 480 pixels in the horizontal direction and 800 pixels in the vertical direction. One of the images was used as a registration image and the other images were used as collation images, and receiver operating characteristics (ROC) were calculated. Thus, the comparison of authentication accuracy was performed. Condition 1 is a condition that the skin authentication is performed using a known minutiae method. Condition 2 is a condition that the skin authentication is performed using the sweat pore-related information. Condition 3 is a condition that the skin authentication is performed using both the minutiae method and the sweat pore-related information. Test results of Conditions 1 to 3 are respectively shown as results 35 to 37 in FIG. 24. As shown in FIG. 24, when comparing Conditions 1 to 3, in comparison to Condition 1 (the result 35), Condition 2 (the result 36) shows a superior authentication performance. From this, it was verified that the sweat pore-related information can improve the authentication performance of the existing authentication method. In comparison to Condition 1 (the result 35), Condition 3 (the result 37) shows a superior authentication performance. From this, it was verified that the authentication performance of the existing authentication method can be improved by combining the sweat pore-related information with the existing authentication method.

Second Evaluation Test

An evaluation test was conducted to verify whether an authentication speed is improved by extracting the pair candidates using the attribute information. A condition that the pair candidates are extracted using the attribute information (a condition that the processing at S214, S216 and S217 in FIG. 17 is performed), and a condition that the pair candidates are not extracted using the attribute information (a condition that the processing at S214, S216 and S217 in FIG. 17 is not performed) were set, and other conditions were set to be the same. The authentication information processing was performed using the same fingerprint image database. As a result, under the condition without the attribute information, 33 minutes and 41 seconds were required for the authentication, and under the condition with the attribute information, 2 minutes and 12 seconds were required for the authentication. An equal error rate (EER) indicating the authentication performance was the same for both the condition without the attribute information and the condition with the attribute information. From this, it was verified that, as a result of extracting the pair candidates using the attribute information, a processing speed of the device 10 was 15 times higher, without any deterioration in the authentication performance.

Third Evaluation Test

Figure 25:
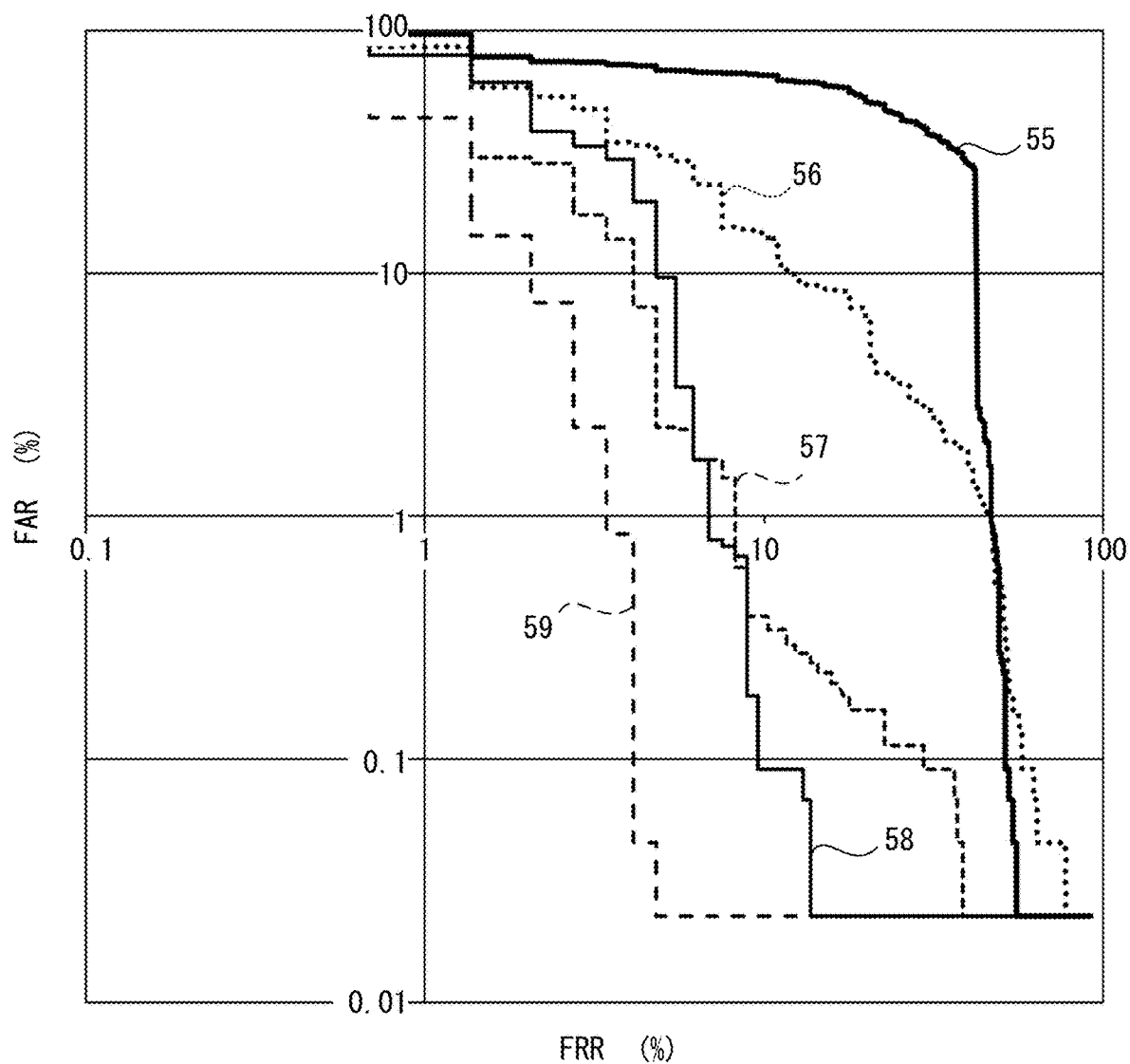
FIG. 25 is a graph showing results of a third evaluation test.

An evaluation test was conducted to verify whether the authentication performance is improved by narrowing down the pair candidates using the image information. In the same manner as in the first evaluation test, for each of Conditions 11 to 15 to be described below, the optical touch sensor was used to acquire 5 to 10 images per finger for 31 fingers, each being an image of 2000 dpi having 480 pixels in the horizontal direction and 800 pixels in the vertical direction. One of the images was used as a registration image and the other images were used as collation images, and the ROC were calculated. Thus, the comparison of authentication accuracy was performed. Condition 11 is a condition that the pair candidates extracted by the processing at S200 in FIG. 16 are not narrowed down (namely, a condition that the processing at S202 to S204 is not performed). Condition 12 is a condition that the pair candidates extracted by the processing at S200 are narrowed down using the image information (the rotation angle) (namely, a condition that the processing at S202 is performed and the processing at S203 and S204 is not performed). Condition 13 is a condition that the pair candidates extracted by the processing at S200 are narrowed down using the image information (the rotation angle) and the score (namely, a condition that the processing at S202 and S203 is performed and the processing at S204 is not performed). Condition 14 is a condition that the pair candidates extracted by the processing at S200 are narrowed down using the positional relationships of the plurality of sets of pair candidates (namely, a condition that the processing at S202 and S203 is not performed and the processing at S204 is performed). Condition 15 is a condition that the pair candidates extracted by the processing at S200 are narrowed down by the processing at S202 to S204. Results of Conditions 11 to 15 are respectively shown as results 55 to 59 in FIG. 25. As shown in FIG. 25, when comparing Conditions 11 to 15, in comparison to Condition 11 (the result 55), Condition 12 (the result 56) shows a superior authentication performance. In comparison to Condition 12 (the result 56), Condition 13 (the result 57) shows a superior authentication performance. From this, it was verified that, in comparison to when the pair candidates are not narrowed down using the image information, the authentication performance can be improved by performing the processing at S202 and narrowing down the pair candidates using the image information, and the authentication performance is further improved by performing the processing at S203 in addition to the processing at S202. In comparison to Condition 11 (the result 55), Condition 14 (the result 58) also shows a superior authentication performance. From this, it was verified that, in comparison to when the pair candidates are not narrowed down by the processing at S204, the authentication performance can be improved by narrowing down the pair candidates by the processing at S204. Furthermore, in comparison to Condition 12 to Condition 14, Condition 15 (the result 59) shows a superior authentication performance. From this, it was verified that the authentication performance can be improved by performing the processing at S204 in addition to the processing at S202 and S203, in comparison to when the processing at S202 and S203 and the processing at S204 are independently performed.

When a processing time under Condition 11 was taken as a reference (0 seconds), processing times under Conditions 13 to 15 were 5.4 milliseconds, 18.5 milliseconds and 10.9 milliseconds, respectively. The processing time under Condition 12 was approximately one hundredth of the processing time under Condition 14. The processing time required for Condition 14 was more than three times the processing time under Condition 13. Although the processing time under Condition 15 is approximately twice the processing time under Condition 13, it is smaller than the processing time under Condition 14. From this, it was verified that both the speeding up of the authentication processing and the improvement in the authentication performance were realized by narrowing down the pair candidates stepwise in order from S202 to S204.

With the above-described authentication information processing device 10 of the second embodiment, the image information can be used to narrow down the pair candidates of the collation authentication information and the registration authentication information used to calculate the degree of similarity. By performing relatively simple processing using the image information, the authentication information processing device 10 can remove the pair candidates that are assumed not to be appropriate as the pair candidates, from among the pair candidates extracted by comparing local arrangements of the plurality of base points in the image. Therefore, the authentication information processing device 10 can improve authentication performance in comparison with related art.

The authentication information processing device 10 calculates the degree of similarity between the collation authentication information and the registration authentication information, using the correspondence between the collation authentication information and the registration authentication information determined by the processing at S205 (S206). Therefore, the authentication information processing device 10 can calculate the degree of similarity using the correspondence determined on the basis of the pair candidates narrowed down using the image information. The authentication information processing device 10 can calculate the degree of similarity on the basis of the correspondence that does not include the pair candidates that are assumed not to be appropriate as the pair candidates.

The authentication information processing device 10 narrows down the pair candidates such that the image information thereof falls within the predetermined range that is set on the basis of the representative value of the image information of the plurality of sets of pair candidates acquired at S201 (S202). Therefore, the authentication information processing device 10 can favorably narrow down the pair candidates on the basis of whether or not the image information of each of the pair candidates falls within the predetermined range set on the basis of the image information of the plurality of sets of pair candidates. Therefore, the authentication information processing device 10 can improve authentication performance in comparison with related art.

The biometric information is the skin information, and the base points are points representing the sweat pores on the ridges of the skin. The related information is information indicating, for each of the plurality of base points, relationships between the target base point among the plurality of base points and a plurality of the base points extracted with respect to the target base point in accordance with the predetermined condition. Therefore, with respect to the related information about the base points representing the sweat pores, the authentication information processing device 10 can narrow down the pair candidates. The arrangement of sweat pores on the ridges of the skin is unique, in the same way as a fingerprint or a voiceprint, and is said not to change over the period of a whole lifetime. Even when the size of the image that represents the skin information is smaller than in related art and the branch points and endpoints of the ridges are not included in the image, there is a possibility that a plurality of the sweat pores can be acquired. Therefore, even when the size of the image representing the skin information is smaller than in related art, the authentication information processing device 10 can achieve both the maintenance of the authentication accuracy and the reduction in processing time of the skin authentication.

In the authentication information processing device 10, when the target base point of the plurality of base points is set as the central base point and the predetermined number of base points arranged around the central base point are set as the peripheral base points, the extraction condition of the peripheral base points is the condition that the predetermined number of peripheral base points are extracted that satisfy the conditions that the distance from the central base point is less than the predetermined value, the number of troughs between adjacent two of the ridges of the skin positioned between the central base point and each of the peripheral base points is equal to or less than 1, and angles formed between line segments connecting the central base point and each of the peripheral base points are each equal to or more than a predetermined angle. The related information includes the information that associates the attribute information indicating the feature of the arrangement on the image of each of the predetermined number of peripheral base points with the position information on the image of the central base point. The authentication information processing device 10 extracts the pair candidates on the basis of whether the attribute information associated with the collation base points matches the attribute information associated with the registration base points (S200). The authentication information processing device 10 acquires the pair candidates extracted at S200 and the image information of the extracted pair candidates (S201). Therefore, using the image information, the authentication information processing device 10 can narrow down the pair candidates extracted on the basis of the attribute information. The attribute information is information indicating the feature of the arrangement of a predetermined number of sweat pores around a target sweat pore, and it can be said that it is information that emphasizes characteristic sections of the biometric information represented by the image. Therefore, by executing the authentication information processing program in this case, the authentication information processing device 10 can efficiently extract the pair candidates in a relatively short time using the attribute information.

The authentication information processing device 10 further narrows down the pair candidates by comparing at least one selected from the group of lengths and angles of line segments connecting each of the central base points of a plurality of sets of the pair candidates that are arbitrarily selected from among the pair candidates narrowed down by the processing at S202 (S204). From among the pair candidates narrowed down by the processing at S204, the authentication information processing device 10 determines the correspondence between the collation related information and the registration related information used to calculate the degree of similarity (S205). Since the authentication information processing device 10 performs the processing at S204, in comparison to when the processing at S202 only is performed without performing the processing at S204, it is possible to narrow down the pair candidates with relatively simple processing, while taking positional relationships with the other base points into consideration. Therefore, the authentication information processing device 10 can improve authentication performance in comparison with related art.

The device 10 can determine the correspondence between the collation authentication information and the registration authentication information used to calculate the degree of similarity in a shorter time, in comparison to when the correspondence is determined by comparing all the base points included in the authentication information. When the pair candidates are not extracted using the attribute information, the CPU 1 omits the processing at S214, S216 and S217 in FIG. 17, for example, and calculates the score and the rotation angle for all the combinations of the collation base points and the registration base points, while taking the influence of the rotation and contraction of the image into consideration, thus determining the pairs. In this case, in the above-described specific example, for each of the ninety sets of combinations, it is necessary to perform eight calculations corresponding to the variable N in FIG. 17 (where N is an integer from 0 to 7), while taking the contraction and rotation of the image into consideration. In contrast to this, with respect to thirty-six pair candidates for which the attribute information is a match, from among the ninety sets of combinations, the device 10 of the present embodiment calculates the score and the rotation angle only when there is the match in the attribute information while taking the contraction and rotation of the image into consideration. The processing that calculates the score and the rotation angle takes a relatively long time, as compared to a simple comparison of the attribute information with a relatively small amount of information. In other words, by extracting the pair candidates, the device 10 can shorten the time required until the correspondence between the collation base point and the registration base point is determined.

The attribute information of the present embodiment includes the classification information. On the basis of the classification information, the device 10 can perform the determination step efficiently in a relatively short time. The classification information is information that is unlikely to be affected by the rotation and contraction of the image. The classification information includes the first information indicating the number of the peripheral base points on the same ridge as the central base point, among the predetermined number of peripheral base points. When each of the predetermined number of line segments obtained by connecting the central base point and each of the predetermined number of peripheral base points is defined as the radial line segment, and when each of the predetermined number of line segments obtained by sequentially connecting, around the central base point, the peripheral base points on adjacent two of the radial line segments is defined as the surrounding line segment, the classification information further includes the second information indicating the number of the surrounding line segments on the ridges. As shown in FIG. 6A to FIG. 6J, the classification information favorably indicates differences in the arrangement of the peripheral base points from two viewpoints of the first information and the second information. The device 10 can generate the classification information that can contribute to speeding up the processing that extracts the collation base points and the registration base points that are used in the processing that determines the correspondence between the collation authentication information and the registration authentication information used to calculate the degree of similarity of the authentication information. In the present embodiment, only when the classification information is a match (yes at S214) is it determined whether or not the other pieces of attribute information (the radial information and the surrounding information) match each other, while taking the contraction and rotation of the image into consideration (S216 to S223). Thus, the CPU 1 can avoid a situation in which the processing that determines whether the attribute information is a match while taking the contraction and rotation of the image into consideration is performed for combinations for which there is no possibility of matching of the other attribute information. Thus, the CPU 1 can shorten the processing time.

The attribute information of the present embodiment includes the radial information, which is the information indicating, for each of the peripheral base points, whether the central base point and the peripheral base point are on the same ridge (S44). In the pair candidate extraction processing, it is determined whether the radial information associated with the acquired collation base points matches the radial information associated with the registration base points, while taking account of all the combinations, which are obtained while taking the influence of the contraction and rotation of the image into consideration, of the arrangement of the peripheral base points with respect to the central base point for collation and the arrangement of the peripheral base points with respect to the central base point for registration (S216). On the basis of the radial information, the device 10 can determine whether the attribute information associated with the collation base points matches the attribute information associated with the registration base points, while taking into consideration the influence of the rotation and contraction of the skin information at the time of acquisition.

The attribute information includes the surrounding information. When each of the predetermined number of line segments obtained by connecting the central base point and each of the predetermined number of peripheral base points is defined as the radial line segment and when each of the predetermined number of line segments obtained by sequentially connecting, around the central base point, the peripheral base points on adjacent two of the radial line segments is defined as the surrounding line segment, the surrounding information is the information indicating, for each of the peripheral base points taken as the starting point of the surrounding line segment, whether the surrounding line segment is on the ridge. In the pair candidate extraction processing, it is determined whether the surrounding information associated with the acquired collation base points matches the surrounding information associated with the registration base points, while taking account of all the combinations, which are obtained while taking the influence of the rotation and contraction of the image into consideration, of the arrangement of the peripheral base points with respect to the central base point for collation and the arrangement of the peripheral base points with respect to the central base point for registration (S217). On the basis of the surrounding information, the device 10 can determine whether the attribute information associated with the collation base points matches the attribute information associated with the registration base points, while taking into consideration the influence of the rotation and contraction of the skin information at the time of acquisition.

The related information (the sweat pore-related information) includes the peripheral information, which is the information based on the position information of the predetermined number of peripheral base points, in addition to the position information of the central base point and the attribute information. With respect to the extracted pair candidates, the device 10 compares the peripheral information included in the sweat pore-related information and determines the correspondence between the collation authentication information and the registration authentication information (S202 to S205). The device 10 can determine the correspondence between the collation authentication information and the registration authentication information, by comparing the peripheral information of the pair candidates. The device 10 of the present embodiment determines the correspondence on the basis of the score and the rotation angle that are calculated on the basis of the peripheral information. Therefore, using the relatively simple processing, the device 10 can efficiently and effectively determine the correspondence.

The device 10 calculates the degree of similarity between the collation authentication information and the registration authentication information, using the correspondence between the collation authentication information and the registration authentication information determined by the processing at S202 to S205 on the basis of the image acquired from the biometric information acquisition device 8 (S206). The device 10 can perform the processing from the generation of the authentication information to the calculation of the degree of similarity, in a relatively short time, in the single device.

An authentication information processing method, an authentication information processing device and a non-transitory computer-readable medium of the present disclosure are not limited to the above-described embodiments, and various modifications may be made without departing from the spirit and the scope of the present disclosure. For example, the following modifications (A) to (C) may be made as appropriate.

(A) The configuration of the device 10 may be changed as appropriate. For example, the device 10 is not limited to a smart phone, and may be a mobile device, such as a notebook PC, a tablet PC or a mobile telephone, for example, or may be a device such as an automated teller machine (ATM) or an entrance and exit management device. The biometric information acquisition device 8 may be provided separately from the device 10. In this case, the biometric information acquisition device 8 and the device 10 may be connected by a connection cable, or may be wirelessly connected, such as with Bluetooth (registered trademark) or near field communication (NFC). The detection method of the biometric information acquisition device 8 may be, for example, an electric field method, a pressure method or an optical method. The biometric information acquisition device 8 is not limited to the surface type and may be a linear type. The size, the color information and the resolution of the image generated by the biometric information acquisition device 8 may be changed as appropriate, as long as the sweat pores can be extracted. Therefore, for example, the color information may be information corresponding to a color image, as well as information corresponding to a white and black image. The device 10 need not necessarily be provided with the biometric information acquisition device 8.

(B) The authentication information processing program may be stored in a storage device of the device 10 until the device 10 executes the program. Therefore, the method by which the authentication information processing program is acquired, the route by which the authentication information processing program is acquired, and the device in which the authentication information processing program is stored may each be changed as appropriate. An information processing program, which is executed by the processor of the device 10, may be received from another device through a cable or wireless communications, and may be stored in a storage device such as a flash memory or the like. The other device may be, for example, a personal computer (PC) or a server that is connected through a network. The storage device is not limited to the ROM 2 and the flash memory 4, and may be a non-transitory storage medium, such as an HDD and an SSD. It is sufficient that the storage device is a storage medium that can store information regardless of the period during which the information is stored. The non-transitory storage medium need not necessarily include a transitory storage medium (for example, a transmission signal).

(C) The respective steps of the authentication information processing need not necessarily be performed by the CPU 1, and some or all of the steps may be performed by another electronic device (for example, an ASIC). The respective steps of the above-described processing may also be performed through distributed processing by a plurality of electronic devices (for example, a plurality of CPUs). The order of the respective steps of the authentication information processing of the above-described embodiments can be changed if necessary, and the steps can be omitted or added. A case in which an operating system (OS) or the like that is operating on the device 10 performs part or all of the actual processing on the basis of commands from the CPU 1 of the device 10, and the functions of the above-described embodiments are realized by that processing, also falls within the scope of the present disclosure. For example, modifications hereinafter described in paragraphs (C-1) to (C-4) may also be added to the authentication information processing as appropriate.

(C-1) The biometric information for acquiring the authentication information need not necessarily be generated by the device 10. In case the related biometric information is generated by the device 10, a configuration of the biometric information acquisition device 8 may be changed as appropriate in accordance with an acquired biometric information. The biometric information may be a fingerprint, an iris, a vein pattern or the like. The base point may be a point that represents the feature of the biological information. For example, when the biometric information is a fingerprint, the base point may be a feature point extracted by the known minutiae method. As long as the base point is a point representing the sweat pore, the base point need not necessarily be the area centroid of the sweat pore. When the device 10 acquires the image representing the biometric information, pre-processing may be performed, as appropriate, on the image acquired at S11. For example, filtering processing may be performed in order to remove high frequency components of the image as noise. As a result of performing the filtering processing, gradation changes in edge portions of the image become moderate. At least one selected from the group of a known low pass filter, a Gaussian filter, a moving average filter, a median filter and an averaging filter may be used as a filter used for the filtering processing. In another example, the filtering processing to extract specific frequency band components only may be performed on the image acquired at S11. A band including a ridge and trough period of the fingerprint may be selected as the specific frequency band. In this case, a known band-pass filter can be taken as an example of the filter used for the filtering processing.

(C-2) The related information need not necessarily be generated by the device 10. When the related information is generated by the device 10, the method for generating the related information may be changed as appropriate in accordance with the biometric information to be acquired. When the biometric information is the skin information and the base points are the points representing the sweat pores, the related information may be, for example, information indicating line segments connecting a plurality of the base points arranged on the same ridge, along the ridge. The pair candidates need not necessarily be determined by the device 10. The method for determining the pair candidates may be changed as appropriate. The processing at S203 and S204 may be changed as appropriate. Processing to narrow down the pair candidates, other than the processing at S203 and S204, may be performed between S202 and S205. The image information may be the movement amount between the collation image and the registration image, or may be the rotation amount and the movement amount. It is sufficient that the processing at S202 be processing that narrows down the pair candidates by comparing the image information of a plurality of sets of combinations of the collation related information and the registration related information. When the image information is the movement amount, for example, a difference between the position information of the collation base point and the position information of the registration base point may be calculated as a parallel displacement amount and stored at S221. In another example, at S221, affine transformation or the like may be used to calculate the movement amount while taking the rotation of the image into consideration on the basis of the position information of the collation base point and the position information of the registration base point, and the calculated movement amount may be stored. At S201, the movement amount may be acquired as the image information. At S202, in the same manner as when the image information is the rotation angle, the pair candidate for which the movement amount acquired at S201 is significantly different from the other pair candidates may be removed, and the pair candidates may be narrowed down to those that are similar to the other pair candidates. When comparison with the other pair candidates is performed, the predetermined range, the representative value and the like may be set as appropriate. The method for calculating the image information may be changed as appropriate. It is sufficient that the processing at S204 be processing that further narrows down the pair candidates by comparing at least one selected from the group of the lengths and the angles of the line segments connecting each of the central base points of a plurality of sets of the pair candidates that are arbitrarily selected from among the pair candidates narrowed down by at least the processing at S202. The number of the pair candidates in the processing at S204 may be changed as appropriate. The method for calculating the length of the line segment (the distance between the base points) and the method for calculating the angle may be changed as appropriate.

(C-3) The sweat pore-related information need not necessarily be generated for all the base points determined from the image. The extraction conditions (the predetermined angle, the predetermined number, the predetermined conditions and the like) of the peripheral base points may be changed as appropriate. It is sufficient that the sweat pore-related information includes at least one type of attribute information. The attribute information may be information, such as the classification information, that does not have the one-to-one association with the peripheral base points, or may be information, such as the radial information and the surrounding information, that has the one-to-one association with the peripheral base points. The classification information may include only the first information or the second information, or may include other information in addition to at least one selected from the group of the first information and the second information. When the classification information includes a plurality of pieces of information including the first information and the second information, the arrangement of each piece of information may be changed as appropriate. The sweat pore-related information need not necessarily include the peripheral information. The method for setting the position information may be changed as appropriate. When the sweat pore-related information includes the peripheral information, as long as the peripheral information is information based on the position information, the peripheral information may include at least one selected from the group of the position information, the angle and the distance, or may include other information that is calculated on the basis of the position information. The method for determining the arrangement order may be changed as appropriate. For example, the arrangement order may be an order of acquisition of the peripheral base points. When comparing the attribute information, the comparison need not necessarily be performed while taking the contraction and rotation of the image into consideration. The order of the processing at S43 to S46 may be changed as appropriate. For example, the processing at S44 and the processing at S45 may be switched in order, or may be performed in parallel with each other. The processing at S43 may be performed after the processing at S44 and the processing at S45.

(C-4) The generated authentication information including the sweat pore-related information need not necessarily be used in the processing that calculates the degree of similarity that is used for skin authentication. After the pair candidates are extracted on the basis of the attribute information of the sweat pore-related information, the method for determining the correspondence in the processing at 202 to S205 may be changed as appropriate. For example, the device 10 may determine the correspondence by comparing the peripheral information or may determine the correspondence on the basis of the arrangement with base points other than the peripheral base points. With respect to the two base points extracted as the pair candidate, the device 10 may determine the correspondence by comparing other information, such as known frequency information (for example, refer to Japanese Laid-Open Patent Publication No. 2017-010419, the relevant portions of which are herein incorporated by reference.) associated with each of the two base points. The skin authentication may be performed by combining the sweat pore-related information with known authentication information. For example, a final determination may be made by combining a collation result obtained by a known minutiae method with a collation result obtained by the authentication method of the present disclosure. In this way, the collation is performed from a variety of viewpoints and an improvement in the collation accuracy is expected. Further, the collation method may be automatically set or settable by the user, from among a plurality of types of collation method, while taking account of the processing time, the authentication accuracy and the like. For example, the final determination may be made by combining collation results by authentication methods that use known frequency information. In this case, it is sufficient that the frequency information be information showing changes in the color around the base point. For example, the frequency components are not limited to a one-dimensional group delay spectrum. For example, other known frequency components, such as an LPC spectrum, a group delay spectrum, an LPC cepstrum, a cepstrum, an autocorrelation function, a cross-correlation function and the like, may be used as the frequency components. The frequency information may be stored in association with the base points.

In this case, the authentication information processing method may further include processing that acquires sample information that is information showing changes in color information around the determined base point, and processing that calculates, as the frequency information, information that associates the frequency components of the acquired sample information with the position information. When the authentication information is stored, the generated sweat pore-related information may be associated with the acquired frequency information, and the associated information may be stored in a storage device as the authentication information. The processing that acquires the sample information and the processing that calculates the frequency information may be performed, for example, between the processing at S25 and the processing at S28 in FIG. 8. In this case, when the degree of similarity is calculated by the authentication information processing method, the degree of similarity, which is a degree of similarity between the sweat pore-related information and the frequency information for collation and the sweat pore-related information and the frequency information for registration, may be calculated on the basis of the determined correspondence. The method for calculating the score and the method for calculating the degree of similarity may be changed as appropriate. At S202, the pair candidates may be narrowed down on the basis of at least one selected from the group of the rotation angle and the movement amount of the collation image with respect to the registration image. The processing at S205 may be omitted as appropriate.

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:

1. An authentication information processing method for an authentication information processing device including a processor and a memory, the authentication information processing method comprising:

acquiring a plurality of pair candidates and image information for each of the plurality of pair candidates, the each of the plurality of pair candidates being a candidate of a combination of related information for collation and related information for registration extracted from authentication information for collation and authentication information for registration to be used to calculate a degree of similarity, the authentication information for collation and the authentication information for registration being used for biometric authentication, the authentication information for collation and the authentication information for registration including plural pieces of the related information, each of the plural pieces of the related information indicating a relationship between a first plurality of base points extracted in accordance with a predetermined condition from among a second plurality of the base points extracted from an image and representing feature points of biometric information, the image information including at least one selected from a group of a rotation amount and a movement amount between an image for collation and an image for registration calculated from the related information for collation and the related information for registration;

narrowing down the plurality of pair candidates by comparing the acquired image information of the plurality of pair candidates of the related information for collation and the related information for registration; and determining a correspondence between the related information for collation and the related information for registration used to calculate the degree of similarity, from among the narrowed down pair candidates, wherein the narrowing down the plurality of pair candidates includes narrowing down the plurality of pair candidates such that the image information thereof falls within a predetermined range set on the basis of a representative value of the image information of the acquired plurality of pair candidates.

2. The authentication information processing method according to claim 1, further comprising:

calculating the degree of similarity between the authentication information for collation and the authentication information for registration using the determined correspondence between the authentication information for collation and the authentication information for registration.

3. The authentication information processing method according to claim 1, wherein the biometric information is skin information and the base points are points representing sweat pores on ridges of skin, and the related information is information indicating, for each of the first plurality of base points, relationships between a target base point among the first plurality of base points and a third plurality of the base points extracted with respect to the target base point in accordance with the predetermined condition.

4. The authentication information processing method according to claim 3, wherein when the target base point among the first plurality of base points is set as a central base point and a predetermined number of the base points arranged around the central base point are set as peripheral base points, the predetermined condition is a condition that the predetermined number of peripheral base points are extracted that satisfy conditions that a distance from the central base point is less than a predetermined value, a number of troughs between adjacent two of the ridges of the skin positioned between the central base point and each of the peripheral base points is equal to or less than one, and angles formed between line segments connecting the central base point and each of the peripheral base points are each equal to or more than a predetermined angle, the related information includes information that associates attribute information, which indicates a feature of an arrangement on the image of each of the predetermined number of peripheral base points, with position information on the image of the central base point, the authentication information processing method further comprises:

extracting the pair candidates on the basis of whether the attribute information associated with the base points for collation matches the attribute information associated with the base points for registration, and the acquiring includes acquiring the extracted pair candidates and the image information of the extracted pair candidates.

5. The authentication information processing method according to claim 4, further comprising:

further narrowing down the narrowed down pair candidates by comparing at least one selected from a group of lengths and angles of line segments connecting each of the central base points of a plurality of sets of the pair candidates that are arbitrarily selected from among the narrowed down pair candidates, and wherein the determining the correspondence includes determining the correspondence between the related information for collation and the related information for registration used to calculate the degree of similarity, from among the further narrowed down pair candidates.

6. An authentication information processing device, comprising:

a processor; and a memory configured to store computer-readable instructions that, when executed by the processor, instruct the processor to perform processes comprising:

acquiring a plurality of pair candidates and image information for each of the plurality of pair candidates, the each of the plurality of pair candidates being a candidate of a combination of related information for collation and related information for registration extracted from authentication information for collation and authentication information for registration to be used to calculate a degree of similarity, the authentication information for collation and the authentication information for registration being used for biometric authentication, the authentication information for collation and the authentication information for registration including plural pieces of the related information, each of the plural pieces of the related information indicating a relationship between a first plurality of base points extracted in accordance with a predetermined condition from among a second plurality of the base points extracted from an image and representing feature points of biometric information, the image information including at least one selected from a group of a rotation amount and a movement amount between an image for collation and an image for registration calculated from the related information for collation and the related information for registration;

narrowing down the plurality of pair candidates by comparing the acquired image information of the plurality of pair candidates of the related information for collation and the related information for registration; and determining a correspondence between the related information for collation and the related information for registration used to calculate the degree of similarity, from among the narrowed down pair candidates, wherein the narrowing down the plurality of pair candidates includes narrowing down the plurality of pair candidates such that the image information thereof falls within a predetermined range set on the basis of a representative value of the image information of the acquired plurality of pair candidates.

7. The authentication information processing device according to claim 6, wherein the computer-readable instructions further instruct the
processor to perform processes comprising:
calculating the degree of similarity between the authentication information for collation and the authentication information for registration using the determined correspondence between the authentication information for collation and the authentication information for registration.

8. The authentication information processing device according to claim 6, wherein
the biometric information is skin information and the base points are points representing sweat pores on ridges of skin, and
the related information is information indicating, for each of the first plurality of base points, relationships between a target base point among the first plurality of base points and a third plurality of the base points extracted with respect to the target base point in accordance with the predetermined condition.

9. The authentication information processing device according to claim 8, wherein
when the target base point among the first plurality of base points is set as a central base point and a predetermined number of the base points arranged around the central base point are set as peripheral base points, the predetermined condition is a condition that the predetermined number of peripheral base points are extracted that satisfy conditions that a distance from the central base point is less than a predetermined value, a number of troughs between adjacent two of the ridges of the skin positioned between the central base point and each of the peripheral base points is equal to or less than one, and angles formed between line segments connecting the central base point and each of the peripheral base points are each equal to or more than a predetermined angle,
the related information includes information that associates attribute information, which indicates a feature of an arrangement on the image of each of the predetermined number of peripheral base points, with position information on the image of the central base point,
the computer-readable instructions further instruct the processor to perform processes comprising:
extracting the pair candidates on the basis of whether the attribute information associated with the base points for collation matches the attribute information associated with the base points for registration, and
the acquiring includes acquiring the extracted pair candidates and the image information of the extracted pair candidates.

10. The authentication information processing device according to claim 9, further comprising:
further narrowing down the narrowed down pair candidates by comparing at least one selected from a group of lengths and angles of line segments connecting each of the central base points of a plurality of sets of the pair candidates that are arbitrarily selected from among the narrowed down pair candidates, and wherein
the determining the correspondence includes determining the correspondence between the related information for collation and the related information for registration used to calculate the degree of similarity, from among the further narrowed down pair candidates.

11. A non-transitory computer-readable medium storing computer-readable instructions that are executed by a processor provided in an authentication information processing device, the computer-readable instructions, when executed, instructing the processor to perform processes comprising:
acquiring a plurality of pair candidates and image information for each of the plurality of pair candidates, the each of the plurality of pair candidates being a candidate of a combination of related information for collation and related information for registration extracted from authentication information for collation and authentication information for registration to be used to calculate a degree of similarity, the authentication information for collation and the authentication information for registration being used for biometric authentication, the authentication information for collation and the authentication information for registration including plural pieces of the related information, each of the plural pieces of the related information indicating a relationship between a first plurality of base points extracted in accordance with a predetermined condition from among a second plurality of the base points extracted from an image and representing feature points of biometric information, the image information including at least one selected from a group of a rotation amount and a movement amount between an image for collation and an image for registration calculated from the related information for collation and the related information for registration;
narrowing down the plurality of pair candidates by comparing the acquired image information of the plurality of pair candidates of the related information for collation and the related information for registration; and
determining a correspondence between the related information for collation and the related information for registration used to calculate the degree of similarity, from among the narrowed down pair candidates, wherein
the narrowing down the plurality of pair candidates includes narrowing down the plurality of pair candidates such that the image information thereof falls within a predetermined range set on the basis of a representative value of the image information of the acquired plurality of pair candidates.

12. The non-transitory computer-readable medium according to claim 11, wherein
the computer-readable instructions further instruct the processor to perform processes comprising:
calculating the degree of similarity between the authentication information for collation and the authentication information for registration using the determined correspondence between the authentication information for collation and the authentication information for registration.

13. The non-transitory computer-readable medium according to claim 11, wherein
the biometric information is skin information and the base points are points representing sweat pores on ridges of skin, and
the related information is information indicating, for each of the first plurality of base points, relationships between a target base point among the first plurality of base points and a third plurality of the base points extracted with respect to the target base point in accordance with the predetermined condition.

14. The non-transitory computer-readable medium according to claim 13, wherein
when the target base point among the first plurality of base points is set as a central base point and a predetermined number of the base points arranged around the central base point are set as peripheral base points, the predetermined condition is a condition that the predetermined number of peripheral base points are extracted that satisfy conditions that a distance from the central base point is less than a predetermined value, a number of troughs between adjacent two of the ridges of the skin positioned between the central base point and each of the peripheral base points is equal to or less than one, and angles formed between line segments connecting the central base point and each of the peripheral base points are each equal to or more than a predetermined angle, the related information includes information that associates attribute information, which indicates a feature of an arrangement on the image of each of the predetermined number of peripheral base points, with position information on the image of the central base point, the computer-readable instructions further instruct the processor to perform processes comprising:

extracting the pair candidates on the basis of whether the attribute information associated with the base points for collation matches the attribute information associated with the base points for registration, and the acquiring includes acquiring the extracted pair candidates and the image information of the extracted pair candidates.

15. The non-transitory computer-readable medium according to claim 14, further comprises:

further narrowing down the narrowed down pair candidates by comparing at least one selected from a group of lengths and angles of line segments connecting each of the central base points of a plurality of sets of the pair candidates that are arbitrarily selected from among the narrowed down pair candidates, and wherein the determining the correspondence includes determining the correspondence between the related information for collation and the related information for registration used to calculate the degree of similarity, from among the further narrowed down pair candidates.

\* \* \* \* \*